(12) United States Patent
Randall

(10) Patent No.: US 10,863,836 B2
(45) Date of Patent: Dec. 15, 2020

(54) CPAP PILLOW APPARATUS AND METHOD

(71) Applicant: Bret Randall, South Jordan, UT (US)

(72) Inventor: Bret Randall, South Jordan, UT (US)

(*) Notice: Subject to any disclaimer, the term of this patent is extended or adjusted under 35 U.S.C. 154(b) by 1316 days.

(21) Appl. No.: 14/483,834

(22) Filed: Sep. 11, 2014

(65) Prior Publication Data

US 2015/0000042 A1 Jan. 1, 2015

Related U.S. Application Data

(63) Continuation-in-part of application No. 12/701,544, filed on Feb. 6, 2010, now abandoned.

(60) Provisional application No. 62/027,729, filed on Jul. 22, 2014, provisional application No. 61/206,912, filed on Feb. 6, 2009.

(51) Int. Cl.
*A47G 9/10* (2006.01)
*A61F 5/56* (2006.01)
*B68G 15/00* (2006.01)

(52) U.S. Cl.
CPC ............. *A47G 9/10* (2013.01); *A61F 5/56* (2013.01); *B68G 15/00* (2013.01); *Y10T 29/481* (2015.01)

(58) Field of Classification Search
CPC .......... A47G 9/10; A47G 9/007; A47G 13/00; Y10S 5/948; A61F 5/30; A61G 13/121; A61G 15/00; A61G 7/072; A61G 7/1084; A61B 6/04; A47C 20/00

USPC ......... 128/845, 848; 5/652, 636, 644, 655.4, 5/695, 948, 951, 421, 448, 645, 655, 691, 5/953, 655.9, 911, 702, 637, 640, 643, 5/458, 641; 600/1, 2; 607/100, 96, 112, 607/114, 108, 109, 110

See application file for complete search history.

(56) References Cited

U.S. PATENT DOCUMENTS

| 4,768,248 | A | 9/1988 | O'Sullivan |
| 5,363,524 | A | 11/1994 | Lang |
| 6,026,330 | A | * | 2/2000 | Chuang .................. A47G 9/007 5/421 |
| 6,891,078 | B1 | 5/2005 | Dillard |
| 6,913,019 | B2 | 7/2005 | Johns et al. |

* cited by examiner

Primary Examiner — Rachael E Bredefeld
Assistant Examiner — Caitlin A Carreiro
(74) Attorney, Agent, or Firm — Pate Baird, PLLC

(57) ABSTRACT

A pillow relies on a shell containing two types of fill material, one comparatively smaller, granular, and characterized by a comparatively larger spring constant, and another comparatively larger, more chunky in shape, and characterized by a comparatively smaller spring constant. Below a threshold level of force (or pressure, which is force per unit area) the larger, softer, second fill material resists flow of the smaller, harder, stiffer fill material. However, upon application of a force (or pressure) above some threshold, the mixture of the two fill materials will flow to conform the pillow to the shape of a user. The pillow will then substantially stabilize in that shape in the absence of forces above the threshold level.

19 Claims, 27 Drawing Sheets

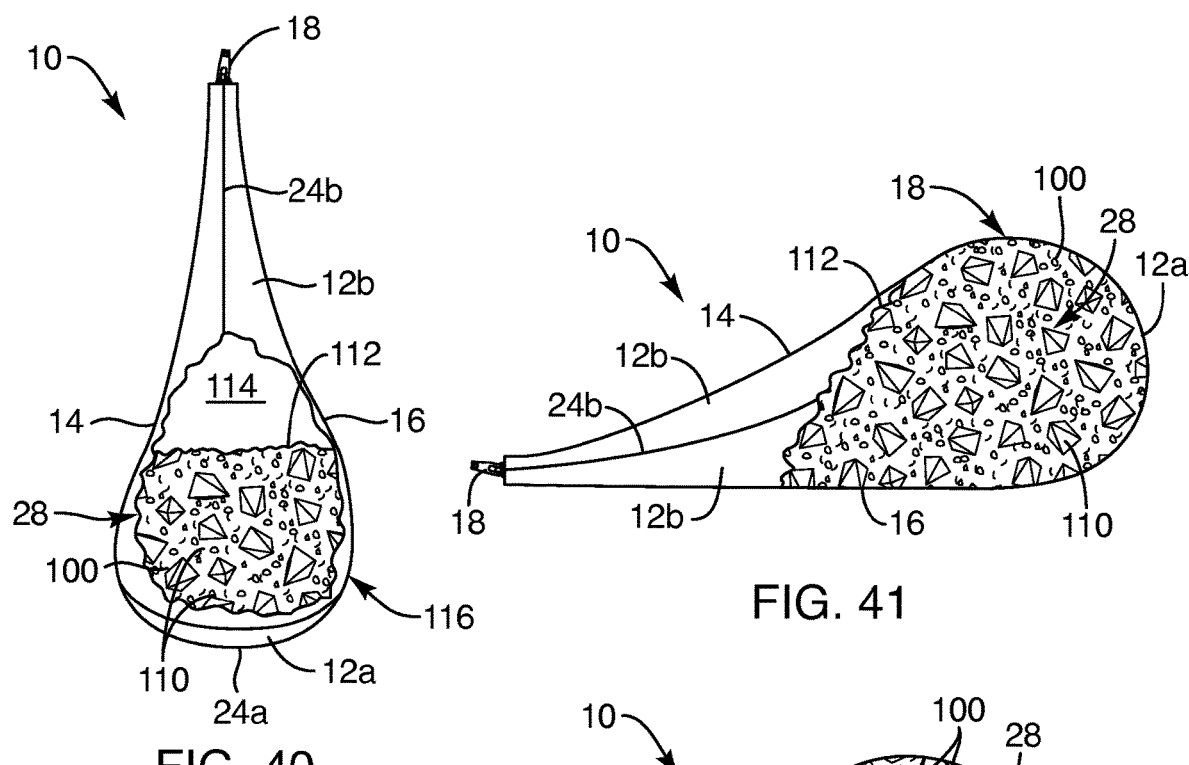
FIG. 40
FIG. 41
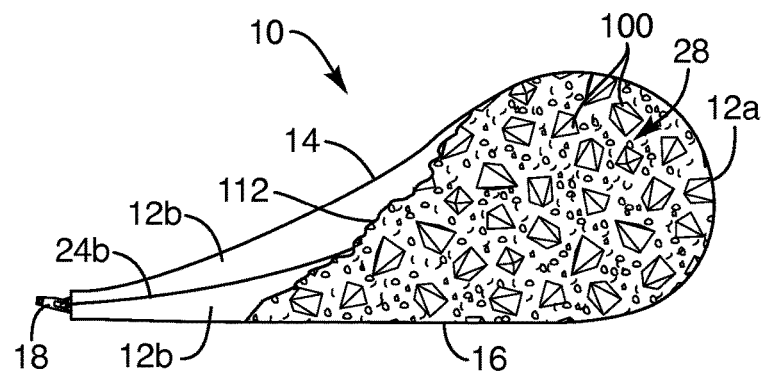
FIG. 42
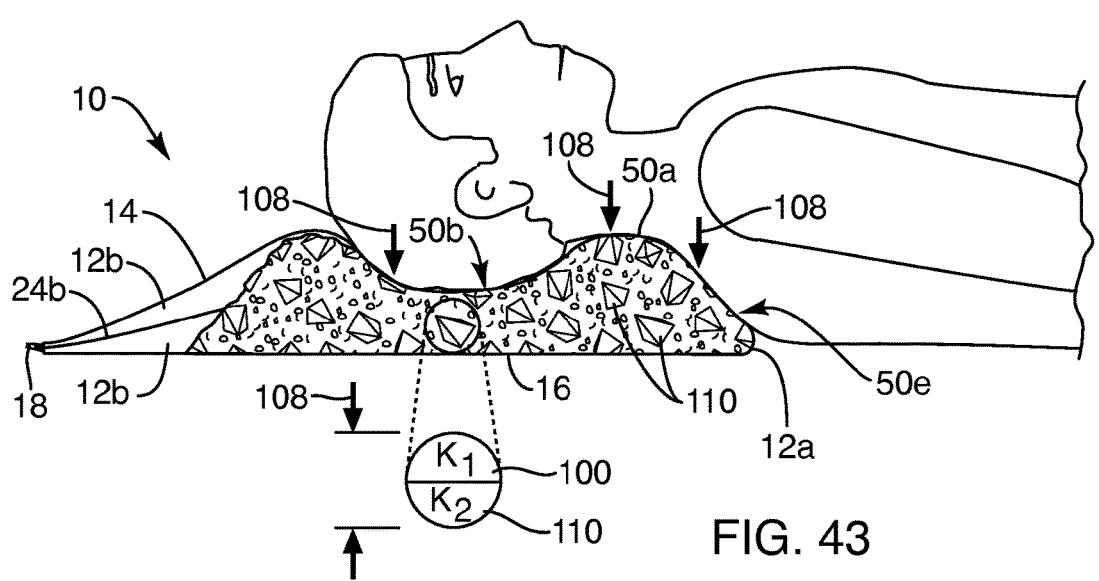
FIG. 43

CPAP PILLOW APPARATUS AND METHOD

RELATED APPLICATIONS

This application: claims the benefit of U.S. Provisional Patent Application Ser. No. 62/027,729, filed Jul. 22, 2014; and is a continuation in part of U.S. patent application Ser. No. 12/701,544, filed Feb. 6, 2010, which claims the benefit of U.S. Provisional Patent Application Ser. No. 61/303,564, filed Feb. 10, 2010; all of which are hereby incorporated by reference in their entirety.

BACKGROUND

1. The Field of the Invention

This invention relates to sleeping apparatus and, more particularly, to novel systems and methods for making and using specialty pillows and adjustable pillow for supporting the body during sleep.

2. The Background Art

Pillows are used during sleep both for comfort and for positioning the head or other bodily member in desired orientations. In the womb and for a period of time after birth, a baby's spine is shaped like a letter C. As the baby develops, secondary curves known as Lordotic develop in the cervical and lumbar regions. These curves continue to develop until growing ceases. In normal spines, four types of spinal curvatures exist, which are important to balance, flexibility, and stress absorption and distribution. The position of the cervical curvature is particularly important in sleep and maintaining the airway open during sleep. Obstruction of the airway during sleep results in snoring and sleep apnea.

One purpose of therapeutic pillows is to position a person's head so as to prevent obstruction of the airway, particularly in the treatment of snoring and mild sleep apnea. Sleep apnea refers to a variety of conditions and syndromes characterized by periods of the temporary cessation of breath, also called apnea.

Obstructive sleep apnea (OSA) refers to apnea syndromes caused primarily by the collapse of the upper airway during sleep. The sleep pattern of an OSA sufferer is characterized by repeated sequences of snoring, breathing difficulty, lack of breathing, waking enough to resume breathing and returning to sleep. Often the sufferer is not consciously aware of the sleep disorder. OSA patients usually experience symptoms characteristic of sleep deprivation such as severe drowsiness, irritability, functional and mental limitations, etc.

The symptoms of snoring and sleep apnea are generally worse for affected people when sleeping in the supine position (lying on the back). In this position, gravity causes the jaw, mandible, tongue muscle, and/or uvula, to move downward, any or all of which may restrict or block the airway. During periods of apnea, breathing ceases and carbon dioxide accumulates in the bloodstream until the central nervous system becomes sufficiently aroused to clear any obstructions. This cycle may repeat hundreds of times in a night for apnea victims. Various pillows using positional means, particularly support of the cervical curvature, attempt to prevent snoring or sleep apnea.

In the case of OSA, a number of medical and surgical treatment options exist. A preferred method of treatment is referred to as Continuous Positive Airway Pressure (CPAP) and other similar devices such as "variable" and "bi-directional" positive airway pressure (collectively referred to as "CPAP"). The effectiveness of this treatment is well documented. CPAP treatment is a common ameliorative treatment for breathing disorders including OSA. CPAP treatment, as described in U.S. Pat. No. 4,944,310, incorporated herein by reference, provides pressurized air or other breathable gas to the entrance of the patient's airway at a pressure elevated above atmospheric pressure. The pressurized air supplied to the patient effectively assists the muscles to keep the patient's airway open, eliminating typical OSA sleep patterns.

NIPPV is another form of treatment for breathing disorders which can involve a relatively higher pressure of gas being provided in the patient mask during the inspiratory phase of respiration and a relatively lower pressure or atmospheric pressure being provided in the patient mask during the expiratory phase or respiration.

Typically, the ventilatory assistance for CPAP or NIPPV treatment is delivered to the patient by way of a nasal mask. Alternatively, a mouth mask or full face mask or nasal prongs are used. In this specification, any reference to CPAP treatment is to be understood as embracing all of the above described forms of ventilatory treatment or assistance.

Breathable gas supply apparatus broadly comprise a flow generator constituted by a continuous source of air or other breathable gas generally in the form of a flower or driven by an electric motor. The electric motor driving the blower is typically controlled by a servo-controller under the control of a micro controller unit. A hospital piped supply can also be used. The gas supply is connected to a conduit or tube, which in turn is connected to a patient mask which incorporates, or has in close proximity, an exhaust to atmosphere for venting exhaled gases.

Typically, the blower and humidifier are separate components connected via a flexible conduit. An air delivery conduit connects the humidifier outlet to a patient interface mask. Alternatively, the blower and humidifier may be rigidly connected together. Air from the blower outlet passes into the humidifier inlet where it is humidified and then passes to the air delivery conduit.

CPAP (and NIPPV) treatment is generally delivered by a mask that interfaces with the patient's nose (nasal mask). One consideration in CPAP treatment is the issue of maintaining the seal between the mask and the patient's face. Whenever that seal is broken, such as through movement during sleep and contact with the patient's pillow, pressurized air from the breathing circuit is lost.

Conventional sleeping pillows made with resilient and pre-loaded materials present problems because the weight of the patient's head causes the pillow in the area of the head to be depressed, leaving the surrounding surface of the pillow to push, unweighted, to a level relatively higher than the head. This results in increased contact between the pillow areas around the patient's therapeutic mask, particularly in side and stomach sleeping positions.

Pillows are of general shapes that have existed for millennia. Moreover, the fill materials and shapes of pillows tend to be traditional. For example, throw pillows may be arbitrarily shaped and covered, and are primarily used for decoration. They may or may not have functional utility. Meanwhile, sleeping pillows are of a typical shape, primarily flat rectangular sheets sewn together. Corners represent a narrowing of cross sectional area as a top surface, meets a bottom surface, while the shared edges come to a theoretical point.

For example, a conventional pillow, may be represented, before filling, by two flat surfaces. These are typically portions of a single sheet of material, folded and sewn or otherwise secured on all sides, that is, at all four edges. Because the material is a single sheet, the seams typically cover three edges, and the fourth is simply a continuous conjoined edge as a result of the fabric itself.

Pillows may be stuffed with a variety of fillings. Typical, or the most common, are synthetic fibers formed as batting. Likewise, some pillows are filled with air, some with shaped or chopped foam, such as latex, urethane, or other polymeric foam. This is sometimes referred to as expanded polymer material (e.g., expanded polystyrene or polystyrene foam) or expanded elastomeric material (e.g., expanded urethane or urethane foam). The most common materials, before the advent of synthetic batting fibers and synthetic foams were natural materials. Natural materials include cotton, straw, feathers, down, and the like.

Pillows, typically, are filled to "overflowing." That is, a pillow case is completely filled with material, and the material is under a certain initial compression. Thus, the pillow will tend to fluff-up and fill-out the pillow case or the cover around the pillow filling material. This gives a pillow a suitable appearance. Likewise, it provides a certain amount of support by virtue of the amount of fill, and its initial force or pressure.

However, a pillow is actually "pre-loaded" such that a certain amount of force is required before the pillow begins to make any appreciable displacement or deflection. By the same token, the amount of pre-load, the amount of force or pressure due to initial deflection, is a function of overfilling and initial displacement. The rate of deflection with respect to a particular force may be used to characterize a pillow.

A fully resilient pillow is problematic in certain circumstances. One of those circumstances is a user wearing a facial apparatus such as continuous positive airway pressure machine or CPAP. Having a resilient pillow means that the pillow will always provide a resistance to compression. The more compression, the more resistance exists.

When a user is trying to sleep, and trying to move freely in sleep, a user may lie on the back, may lie on the side, may lie on the stomach, and may position the head in a variety of positions accordingly. Having a CPAP extending the profile of the face provides both an area and a leverage distance for the pillow to push at the CPAP mask. It is not uncommon for a resilient pillow to break a CPAP mask free from the face of a user. Thus opening the seal that should exist between the CPAP mask and the face of the user renders the CPAP machine ineffective.

Even in matters of comfort alone, it is not uncommon for a resilient pillow, to have its shape and resilience predominantly dictated by its manufacturing. It cannot respond to a user's comfort by being adjustable in profile, thickness, supporting force, and the like about the head, neck and shoulders of a user. Likewise, a pillow applied to another member body, such as to support a leg, lumbar region of the back, or the like may also present discomfort at "pressure points." These result due to the wide range in support pressure at various locations and the lack of a "profile match" between the shape of the body and the shape of the pillow. This is particularly true when combined with the specific resilience or spring force and resulting pressure presented by a resilient pillow pressing on any particular "projection" of the body part selected.

Thus, reliable shapes, fill amounts, and support where needed are simply not available in conventional pillows. Even the best developed granular-fill materials have proven inadequate. Attempts have been made to snap down or restrict certain areas of the pillows in order to limit the migration of granular materials. These have still proven un-satisfactory. They are initially too hard, do not profile the body, and result in loss of support due to fill migration.

What is needed is a pillow that presents no initial pre-load or pressure to fit a bodily profile of a user, regardless of position and in spite of a CPAP mask. What is also needed is a pillow that will naturally migrate materials to the desired location in response to natural movement of a user. Likewise, it would be beneficial to have a granular material that is movable and adjustable directly by a user. However, once the material has been adjusted, it would be an advance in the art to provide a structure for a pillow and a shape thereof along with a method of use in which the continued use of the pillow during a night of sleep would tend to promote the continued proper distribution of the fill material into the right locations to support the supported profile shape, and its maintenance at those locations.

BRIEF SUMMARY OF THE INVENTION

In view of the foregoing, in accordance with the invention as embodied and broadly described herein, a method and apparatus are disclosed in one embodiment of the present invention as including a pillow and method of adjusting a pillow. The method includes providing a shell having a top panel, a bottom panel, a first wall panel connected to both, and a second wall panel opposite the first wall panel and connected to the top and bottom panels. A barrier is formed at a connection between the first wall panel and the top panel and between the first wall panel and the bottom panel. First and second end panels are each fixed to the top, bottom, first wall, and second wall panels. First and second retreat regions are formed by the top, bottom, and first wall, at the connections thereof with the first and second end panels, respectively. With a first quantity of fill and instructions, a user begins by selecting a second quantity of the fill, opening the shell and pouring into the shell that second quantity of fill selected. Thereafter, migrating substantially the entire second quantity of fill toward the first wall panel is accomplished by grasping the pillow away from the first wall panel and lifting and shaking, resulting in free falling of the second quantity of fill material.

Laying the bottom panel on a sleeping surface a user may adjust the location of the fill, forming relief regions by moving portions of the fill therefrom. Applying force to the second quantity through the top panel will flow at least a portion of the fill by disengaging the granules thereof from one another. Tapping, poking, patting, or other means of applying repeated force and dislodgement will urge fill away from a relief region and toward the retreat regions. After forming a desired profile in the pillow, a user may nestle in by placing the head and neck of a user in the relief region and moving a panel down, back and forth, or both. Once the fill fits the bodily profile it will support the head and neck with a substantially uniform pressure exerted by the granules through the top surface.

This system benefits from uncoupling mechanical vibration of fill from the outermost layer proximate a user to deaden sound and reduce initiation thereof. Granules of buckwheat hulls, having projections acting as springs and engaging one another between adjacent granules provide stability. A quilted, cellularized cover bridges the projections to provide a smooth, comfortable surface without abrasion from the fill.

In certain embodiments of an apparatus, composition, and method in accordance with the invention, a method of distributing load more uniformly across a portion of a user on a pillow may include providing a shell defining a cavity to contain a fill, the shell defining a longitudinal direction, a lateral direction, and a transverse direction, orthogonal to each other. The shell may comprise a top and a bottom, each shaped substantially rectangularly, and a first wall secured to the top and bottom and spacing the top and bottom away from one another. The shell may have a joinder, such as a seam, a zipper, a secured but openable system, another wall thinner, or the like, connecting the top and bottom together. Side walls may form second and third walls as triangles.

A quantity of the fill fits within the cavity. The fill may include a mixture of a first filler comprising a granular material (e.g., of plastic granules, buckwheat hulls, or the like) having an effective diameter (hydraulic diameter of 4 times the area divided by the perimeter) less than that of the second filler, and the second filler having a spring constant less than that of the first filler. The larger and softer pieces or particles of the second filler are selected to resist flowing by the first filler in response to a load on the shell, absent a threshold of force or pressure (force per unit area). The filler will flow the second material (soft and large) with the first filler in response to any force meeting the threshold level of force.

As an operational principle, one must put the fill in the cavity in a quantity insufficient to fill the shell, typically less than half the volume of the shell, and extends less than half the distance from the first wall to the joinder when the shell is suspended from the joinder. The fill may be selected and the quantity may be selected to fall freely toward the first wall when the shell is suspended from the joinder.

Use may include moving the quantity of fill toward the first wall by suspending the shell from the joinder, then positioning the shell with the bottom on a sleeping surface. There is a certain amount of sloughing downward and away, by the fill, away from the top and toward the bottom and the joinder.

Setting the pillow up for use on a daily basis may start with loading the fill by positioning a bodily member on the top. This may be followed by increasing the loading above the threshold of force by moving the bodily member and then re-shaping the quantity of fill by its shifting (flowing) in response to the increasing the loading above the threshold value. Load means a force, stress, or pressure, where stress and pressure are force per unit area. Strain is deflection (movement or change of shape) in response to a load.

The re-shaping may include conforming, by the quantity of the fill, to a portion of the user supported thereby. There is initial resisting, by the second filler, any movement by the first filler in response to weighting by the portion of the user supported by the fill. Above the threshold value, both types of fill material will move as a non-homogeneous mixture of a first filler and a second filler, the first filler comprising a granular material having an effective diameter less than that of the second filler, and the second filler having a spring constant less than that of the first filler.

During setup, the user causes a consolidating of the fill, in unobstructed fall toward the first wall, by suspending the shell, containing the fill, from the joinder. After placing the pillow on a sleeping surface with the bottom closest thereto, a user takes his or her place with head, neck, and possibly shoulders on the top, above the fill. This should be done with a dynamic movement to apply a threshold level of force by a portion of the user against the top. The result is flowing, by the first and second fillers, in response to the applying the threshold level of force, to conform to the shape of the portion of the user. Absent such a continuing value of the force, the pillow remains as it is, conserving, by the second filler, the positioning of the first filler and second filler, by resisting flow of the first filler in response to the continual, and lesser, weight of the portion of the user at less than the threshold level of force.

In summary, the pillow has a shell defining a cavity formed to contain a fill, and having a longitudinal direction, a lateral direction, and a transverse direction, orthogonal to each other, with a top, bottom, first wall connecting and spacing apart the top and bottom, and a joinder connecting the top and bottom together opposite the first wall. Inside the shell is the fill, comprising a mixture of a first filler and a second filler, the first filler comprising a granular material having an effective diameter less than that of the second filler, and the second filler having a spring constant less than that of the first filler. Use involves placing the pillow on a sleeping surface, adjusting the shape of the pillow conformal to a user by applying a threshold level of force by a portion of the user against the top, the threshold level of force being selected to be effective to overcome a resistance of the second filler to flow of the first filler in response to loading. Thereafter, the shape may change in response to motion of a user during sleep or otherwise. However, the shape is usually and generally conserved by the second filler (larger and softer) resisting flow of the first filler (smaller and stiffer) to the weight of the portion (bodily members) of the user at less than the threshold level of force, stress, pressure, or other loading.

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

FIG. 40 is a right end elevation view thereof, in a suspended configuration, partially cut away to show the cross section of the fill material within the pillow or the bag that forms the pillow;

FIG. 41 is a right end, cross-sectional, end elevation view thereof, the pillow having been first adjusted to shake the fill material toward the front panel, then being laid with the bottom panel on a supporting surface, and illustrating the boundary of the piled fill material therewithin;

FIG. 42 is a right end, cross-sectional, elevation view thereof illustrating the disposition near the end of the pillow, away from a user, wherein the fill material is pushed up, and partially distributed back away from the panel; and FIG. 43 is right end, elevation, cross-sectional view of a pillow in accordance with the invention with the cross-section taken at a center plane of symmetry corresponding to a user resting on the pillow.

DETAILED DESCRIPTION OF THE PREFERRED EMBODIMENTS

Figure 1:
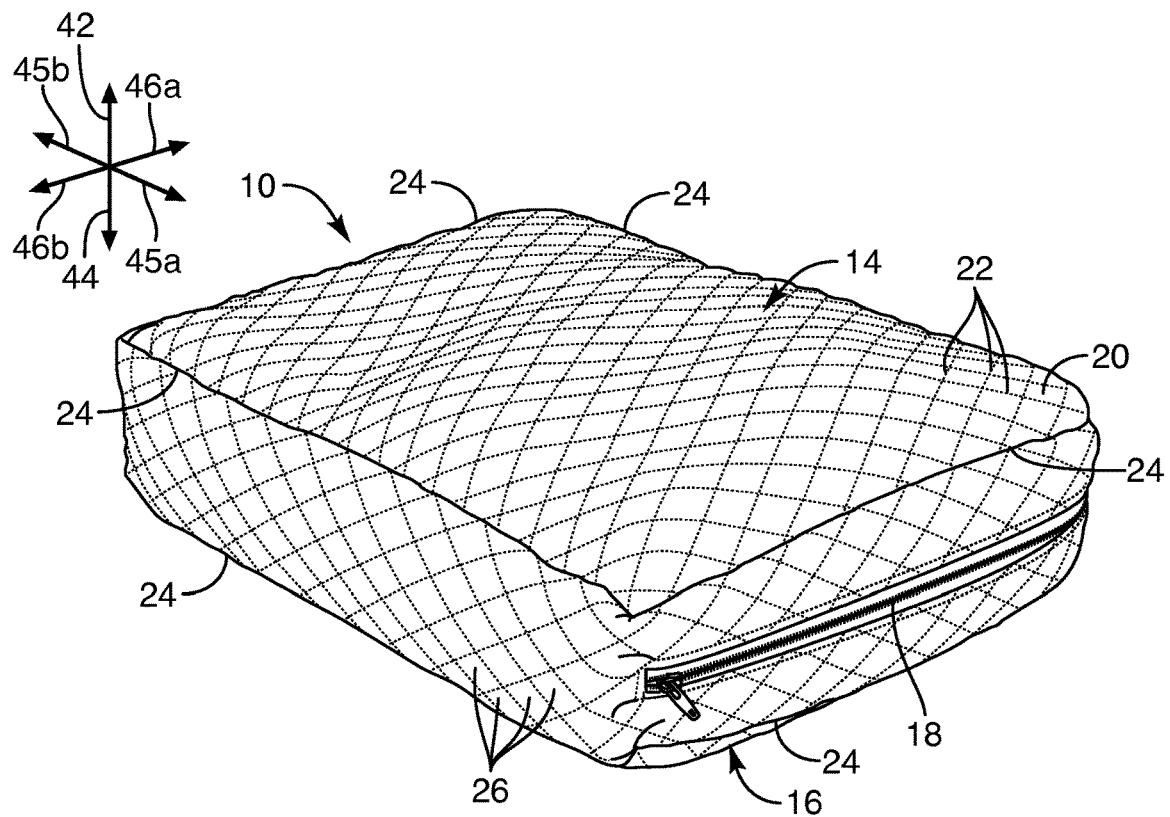
FIG. 1 is an end top quarter perspective view of one embodiment of an apparatus in accordance with the invention.
Figure 2:
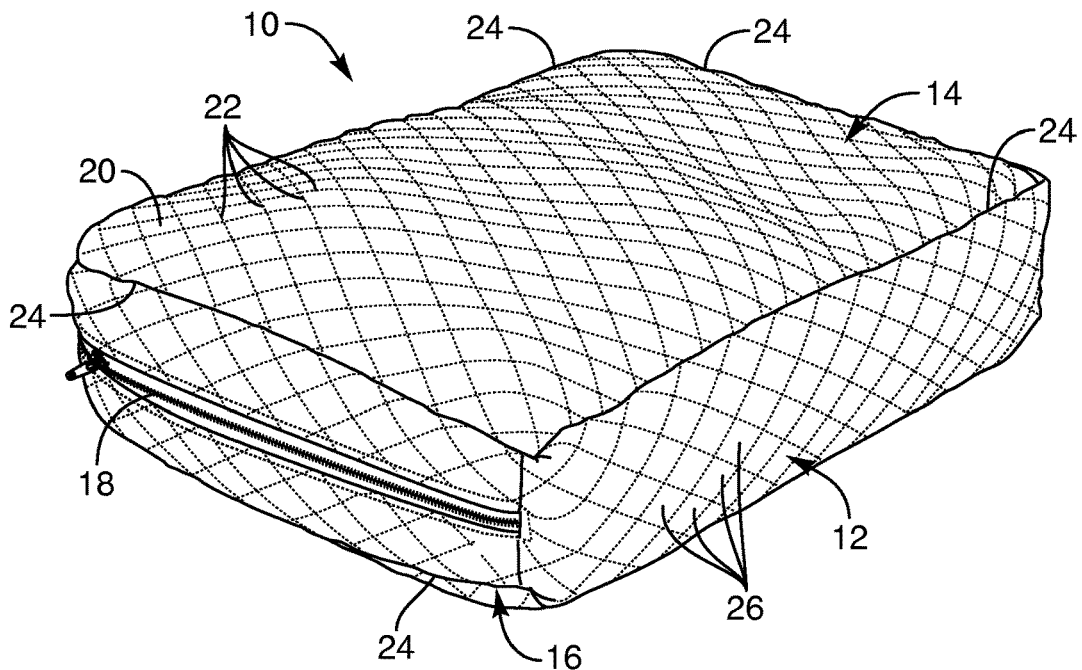
FIG. 2 is an end top quarter perspective view of an apparatus in accordance with the invention as illustrated in FIG. 1.
Figure 3:
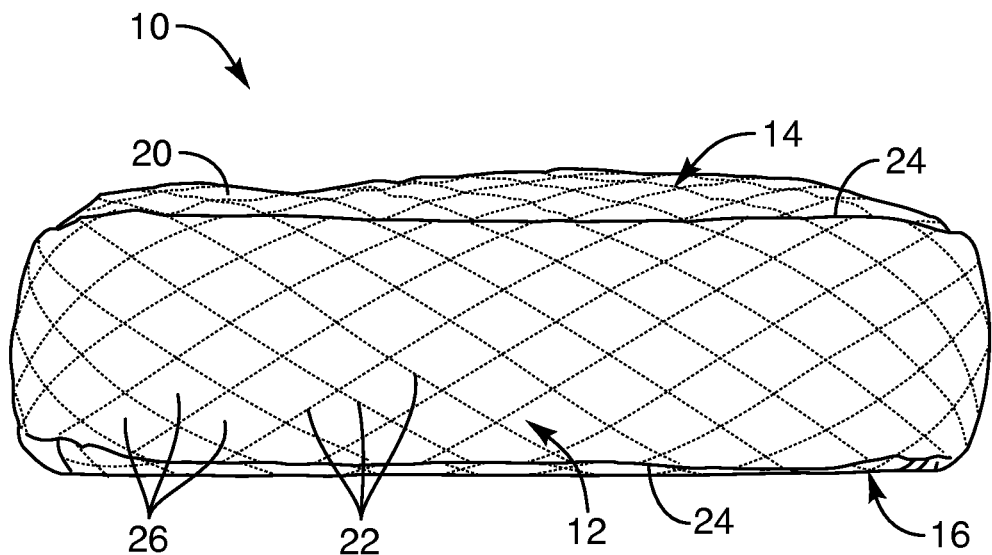
FIG. 3 is an left end elevation view of the apparatus of FIG. 1.
Figure 4:
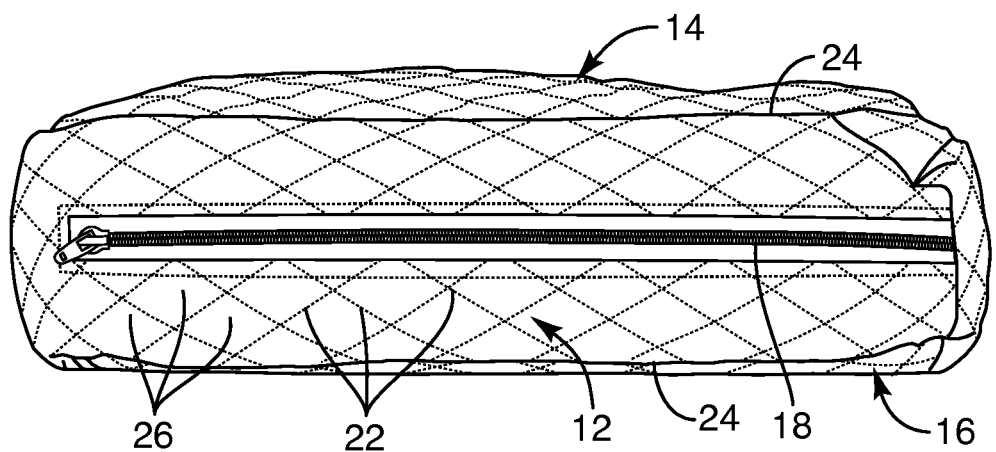
FIG. 4 is a right end elevation view of the apparatus of FIG. 3.
Figure 5:
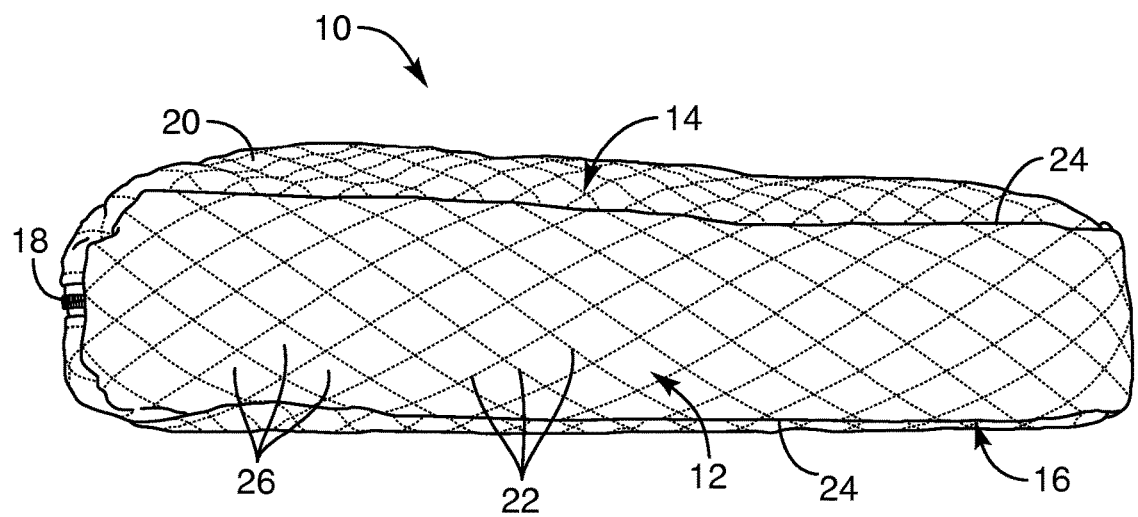
FIG. 5 is a side elevation view of the apparatus of FIG. 1.
Figure 6:
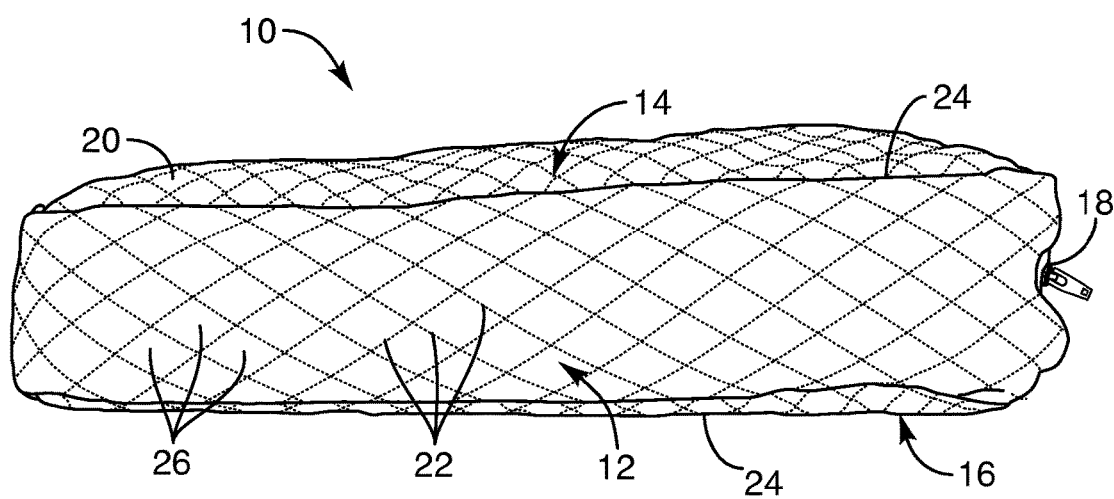
FIG. 6 is the opposite side elevation view of the apparatus of FIG. 1.
Figure 7:
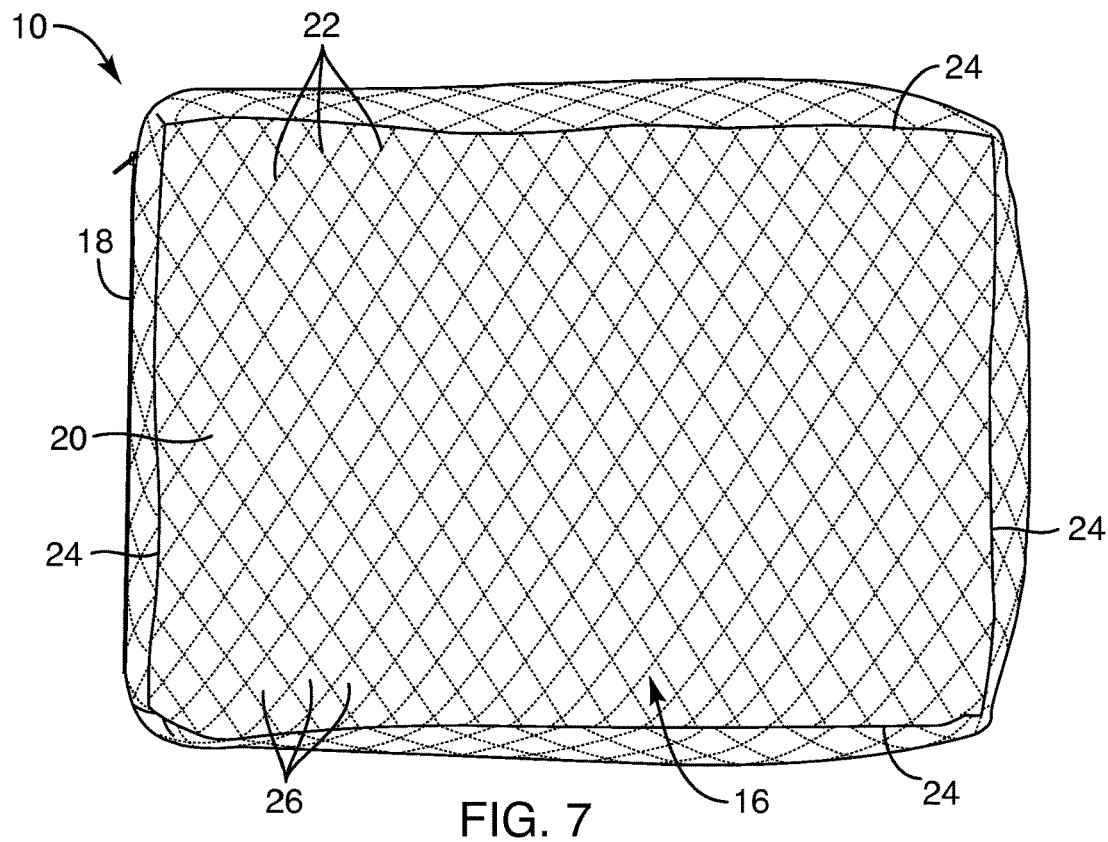
FIG. 7 is a top plan view of the apparatus of FIG. 1.
Figure 8:
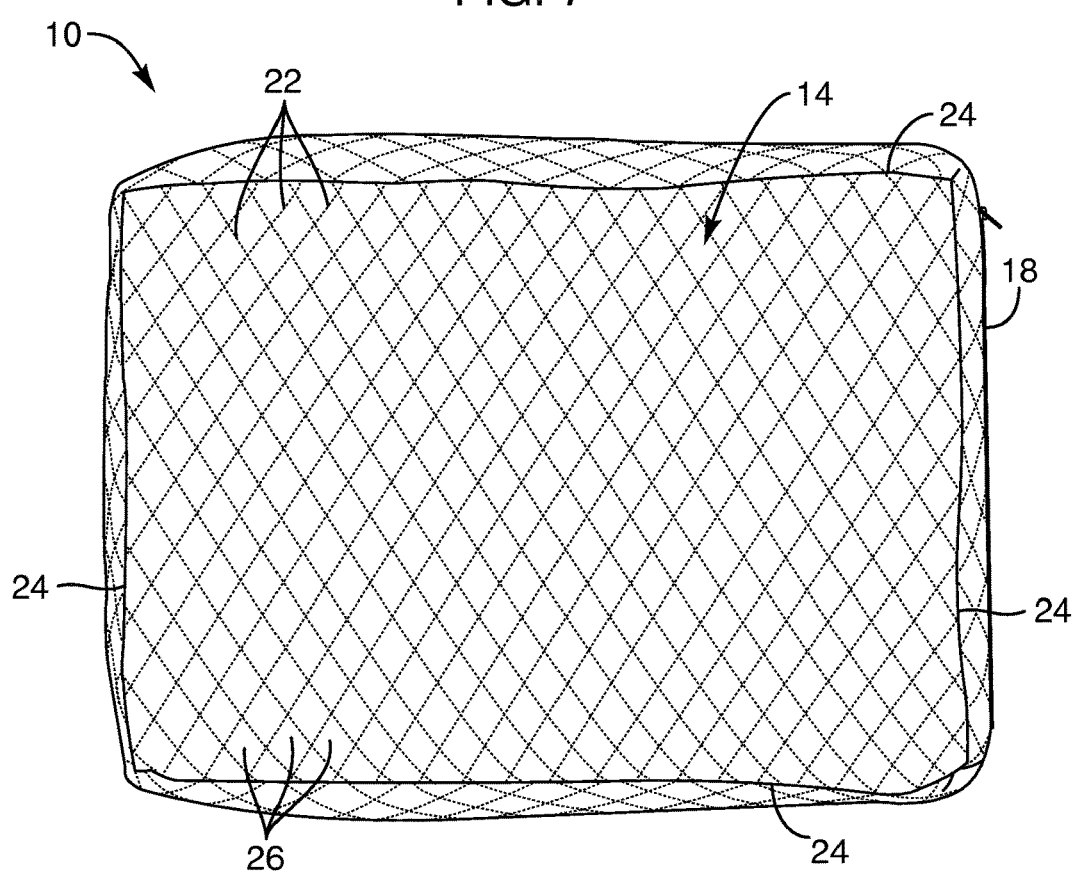
FIG. 8 is a bottom plan view of the apparatus of FIG. 1.

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention, as claimed, but is merely representative of various embodiments of the invention. The illustrated embodiments of the invention will be best understood by reference to the drawings, wherein like parts are designated by like numerals throughout.

A fundamental problem with pillows is found in the exact reason they exist. A pillow is a supporting member. A pillow may be used behind the back supporting the user in a sitting position, such as reading in bed. Likewise, a pillow may be used to elevate the head, neck, shoulders, feet, or the like. Thus, pillows represent support members. Some people prefer a very stiff pillow that maintains its shape. Others prefer a pillow that is softer, responding more to the weight placed thereon.

Pillows typically represent a couple of characteristics that are desirable and relied upon in used. Those two characteristics are the volume and resilience. Resilience is technically defined as the effective spring constant. According to Hooke, as represented by Hookes's Law, a resilient or spring-like material deflects or displaces in direct proportion to the force applied. Thus, a spring may be stretched or may be compressed at a ratio of force to displacement represented by a constant value. In other words, the force of resistance of a spring is directionally proportional to the distance the spring has been compressed ($F=-kx$) or stretched (moved from its equilibrium or unloaded position).

Accordingly, that constant (k) representing the relationship between force (F) and displacement (x) represents a characterization of the stiffness of any spring. Thus, down, feathers, batting, and foam may be characterized according to their effective spring constants. For example, down tends to be comparatively soft. That is, it will deflect or compress with less force or at a higher rate, with respect to a given force, than will feathers. Likewise, foam may be made in a variety of grades, any particular grade engineered to develop a certain amount of resistive or resilient force in response to the application of a particular load. Likewise, batting presents a certain resistance to displacement, characterized by such a relationship.

Materials exist, such as plastic pellets, grains, and other granular materials that have a particularly high resilience when placed in compression. As a granular material most do not represent permanent effective resilience. For example, a bean bag, such as used in games, or a grain bag, such as those preheated for comfort and applied to a member of the body present, comparatively high stiffness as to each individual grain. Each individual grain tends to present substantial resistance against deflection.

On the other hand, two grains, with respect to one another, may move, thus responding to motion or force by changing locations. Once the location is changed, certain grains or pellets will have dropped to a lower level than they previously held. In the presence of gravity, those grains will not rise back to their previous locations. Thus, their displacement becomes permanent, and without the permanent resilience or permanent spring loading that may be present in conventional pillow materials.

However, such granular or non-fibrous fill materials for pillows still present other problems. They do not reconstitute. Their materials shift permanently. Moreover, when those materials shift locations, they do not provide the support in either thickness nor force present in their previous, unmoved locations. On the one hand, this may be a good thing. On the other hand, this represents a problem in control.

Another difficulty with conventional pillows is that their shape tends to promote a certain inclined shape when filled with a fibrous bat. That is, bats, being mechanically interconnected fibers, tend to operate in concert. The pressure of shoulders on the edge of a pillow tends to reduce the entire pillow to an incline progressing from the lowest point under the shoulders near the edge of pillow to a highest point further away. Thus, the neck remains effectively uncontacted and unsupported when the shoulders weight an edge of the pillow.

Similarly, if the shoulders do not weight any part of the pillow, then the neck rests near the edge of the pillow, at the lowest and thinnest part of the pillow. This provides very little support, and often no support. Meanwhile the head represents a protrusion down into the pillow. Yet, the head sits on the "high ground" at the thickest part of the pillow. Thus pillow support is effectively the opposite of what it needs to be.

For example, the neck needs support at its position, which is actually higher (away from a line between head and shoulders) than the back of the head would be in a lying position. Meanwhile, the head, which needs more of a recess or more of a relief position and a lower or thinner support material, is given the opposite instead, the thickest part of the pillow.

Even when one deals with down, which is less fibrous, the problems persist despite not having a continuous mechanical link across the entire width of a pillow between down tufts. The problem is not remediated, for example, with down pillows. Forces may be less, but still persistent. Fill tends to be complete, even though a user may punch the pillow or shake it in order to rearrange the volume. Nevertheless, the fundamental shape of a pillow as two sheets bound on four edges still tends to keep the center overfilled, with corners and edges as the thinnest parts of the pillow, simply because they can hold only what their volume will tolerate. Even if one goes to the materials such as a bean bag or a grain bag, the shape of the pillow results in less material near the edges, and a substantially less material in all corners.

The volume of a cube, for example, is the length of a side raised to the third power ($S^3$). The volume of a sphere is four-thirds the physical constant pi multiplied by the third power of the radius of the containing cube ($\frac{4}{3}\pi r^3$). Thus, one sees that a sphere contains effectively half the volume of a cube having the same maximum side. That is, a cube having a side length of S encompasses twice the volume of a sphere having a diameter equal to that same value of S. Similarly, a cone represents about a quarter of the volume of a rectangle having the same maximum dimensions. Thus, corners of a pillow contain substantially less material than would be contained in a box of the same size.

A sleeping pillow may not generally be made in a box shape. Such would be very uncomfortable. Cushions for couches may typically support their top surfaces in a substantially planar orientation. Also, edge support is comparatively stiff to maintain the shape and support weight of an entire person. Applicant knows of no system in which a sleeping pillow for the head of a user has a parallelepiped (e.g. rectangular axial cross-section) shape.

Meanwhile, a fill material comprising granular materials such as buckwheat hulls has its own problems. Put in the shape of a conventional pillow, a buckwheat hull fill material migrates unacceptably. Attempts to control that migration have been limited by, among other things, the conventionality of the basic shape of a pillow, two sheets bound on their four shared edges. This results in corners that contain only about one-quarter of the volume per projected unit of area of the top surface. That is, were an individual to measure the volume of the corners of a stuffed pillow, they would include only about one-quarter of the volume of a parallelepiped having the same maximum dimensions.

Referring to FIG. 1 through 9, while referring generally to FIGS. 1 through 43, a support 10 or pillow 10 in accordance with the invention may include a frame 12 or a frame portion 12. The frame 12 may be provided with a suitable attachment mechanism, such as sewing or the like, to attach a top 14 or top material 14 and a bottom 16, a bottom material 16 or bottom portion 16 of the pillow 10. In the illustrated embodiment, the pillow may include a closure 18, selectively openable and closable in order to provide access to the interior of the pillow 10.

For example, in one embodiment, the closure 18 may be permanent and formed of stitching, clamps, buttons, or the like. In other embodiments, the closure 18 may be more readily openable, such as a zipper, a hook-and-loop fastener such as Velcro™ fastener, or the like. Typically, the frame 12, as well as the top 14 and bottom 16, may be fabricated of a suitable material 20, such as a fabric 20 having suitable bending flexibility, as well as suitable strength stiffness, and the like "in plane."

In certain embodiments, a non-woven fabric may serve as the material 20. In other embodiments, a woven fabric, whether of synthetic or natural materials may be used to form the portions 12, 14, 16, of the pillow 10. In one embodiment, the material 20 such as a fabric 20 may be provided with seams 22 providing texture. Similarly, the frame 12, top 14, and bottom 16 may be secured to one another structurally by other seams 24.

In the illustrated embodiment, the texture seams 22 may form the material 20 into cells 26. By virtue of the constrictions provided by the seams 22, the material 20 may alternately contain thick portions and thin portions according to a fill within the material 20, or captured between layers of the materials 20 in order to form the cells 26. Thus, the texture seams 22 result in an undulating assembly of cells 26 that provide texture for multiple purposes.

The pillow 10 may be provided with one of various types of fill 28. In one presently contemplated embodiment, the fill may be a quantity of hulls, such as buckwheat hulls. Buckwheat hulls have a unique shape providing a certain amount of resilience, a certain resistance to flow, but yet a discrete granular character that does permit flowing or pouring in order to properly make and use a pillow 10 in accordance with the invention.

Figure 9:
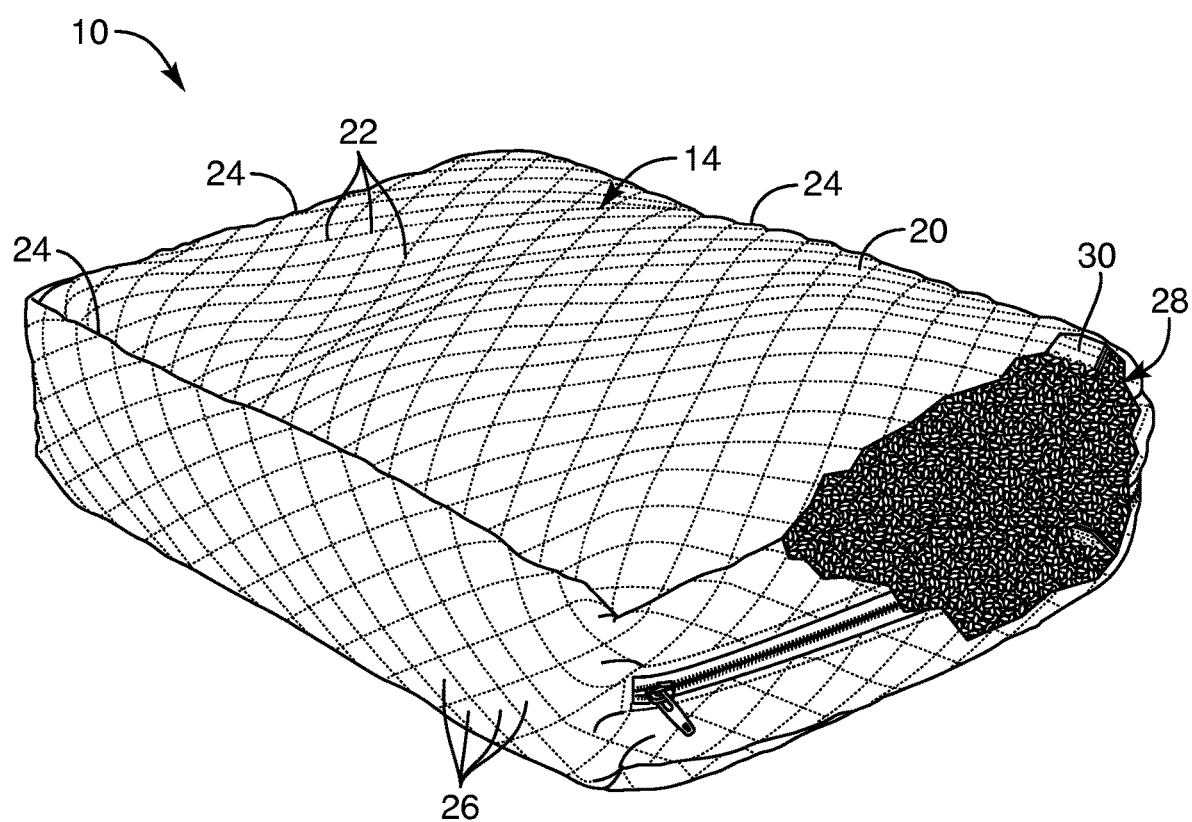
FIG. 9 is a front end quarter perspective view of a cut-away representation of the apparatus of FIG. 1.

Referring to FIG. 9, while continuing to refer generally to FIGS. 1 through 43, the fill 28 may be impeded in its free flow about the interior of the pillow 10 by virtue of barriers 30 formed of the material 20 when sewn together by the structural seams 24. The barriers 30 may be formed to have to a particular length, stiffness, and thickness selected to provide a mechanical barrier 30 resisting movement thereagainst by the fill material 28. Other resistance comes from texturing and interlocking of hulls with one another.

Figure 10:
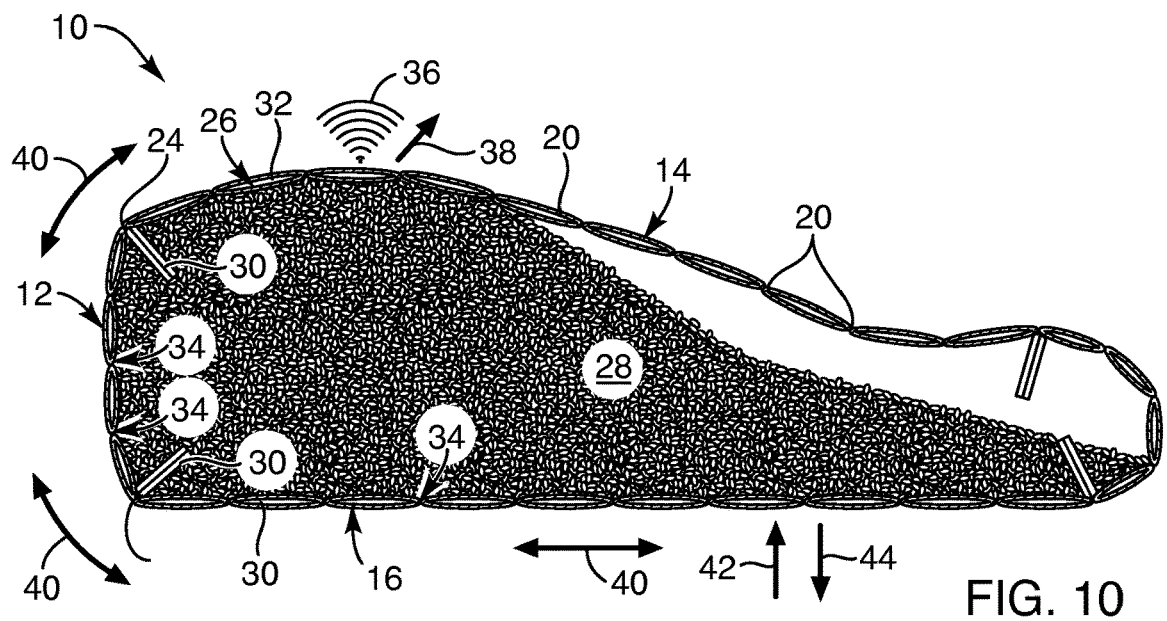
FIG. 10 is a partial, cross-sectional view of the apparatus of FIG. 1 in an embodiment involving a partial fill in accordance with the invention.
Figure 11:
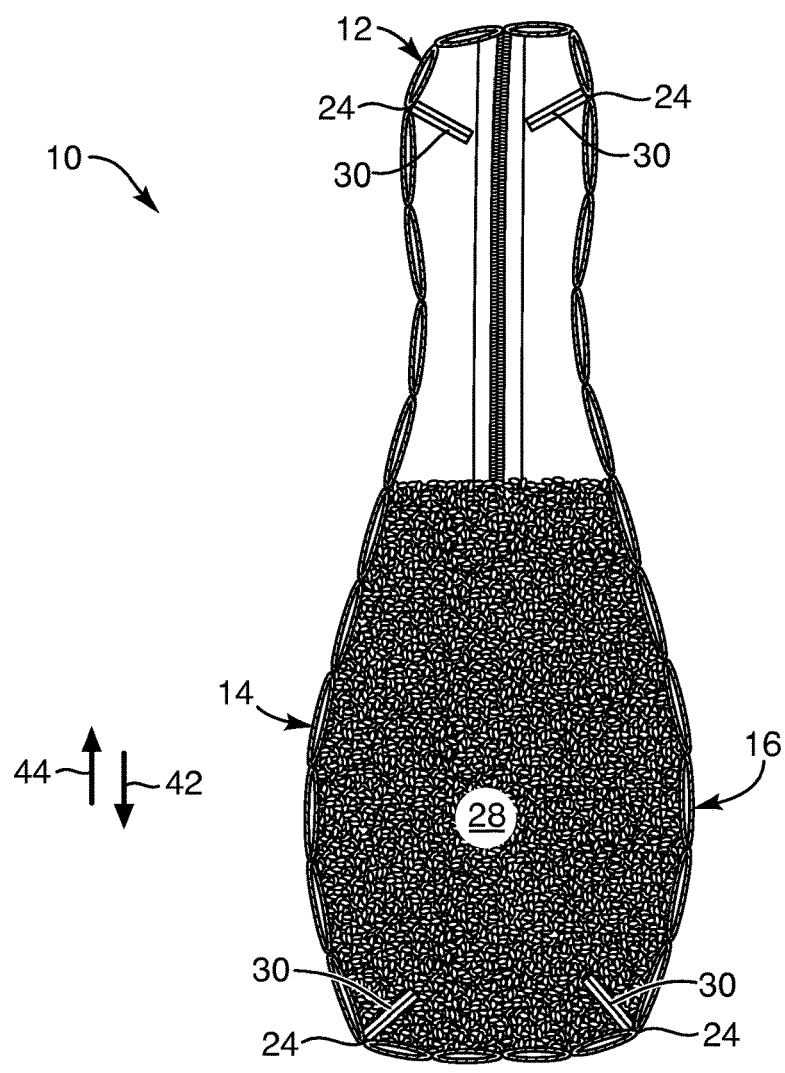
FIG. 11 is an end cross-sectional view of the apparatus of FIG. 1 being prepared for use by urging all of the limited fill material toward one side thereof.

Referring to FIGS. 10 and 11, while continuing to refer generally to FIGS. 1 through 43, the material 20 may be formed of top and bottom layers, filled with a batting 22 therebetween. The functions of batting 32 are multiple. Every child has been told that placing a sea shell to the ear permits one to hear the ocean roar. It has been found that use of materials such as hulls, and other naturally stiff and thin materials results in an inordinate amount of sound originated by and propagated through the material 20 covering the pillow.

Likewise, it has been found that the use of materials that are unconventional as a fill material 28, such as particles having projections, results in projection of the shapes of those fill materials 28 into the material 20. These projections provide a comparatively course and rough texture through and, therefore along the surface of, the material 20. The material 20 needs to be granular, discrete, and needs to have its various thin plate-like shapes. Those shapes provide desired resilience, as well as to provide a certain resistance to motion. Those same projecting shapes result in literally scratching or abrading the face of a user employing a pillow made in accordance with conventional construction techniques.

Therefore, one of the purposes of the batting 32 is to provide a certain selected thickness between the layers of the material 20. This thickness tends to remove the texture that would otherwise appear on the surface of the material 20 in response to the discrete shapes of the fill material 28. Batting 22 also provides filling between projections. Batting also provides structural stiffness in the material 20, resisting bending. This resistance to bending tends to cause the material 20 to span across the distance between projections, thus eliminating the influence thereof outside the pillow 10.

The batting also provides sound deadening by virtue of its distance, thickness, softness, material selection, and mechanical disruption of the mechanical path to the ear. For example, sound travels through the air. Sound will likewise travel through materials. When the fill material 28 is touching directly the outermost layer of the material 20, then the fill 28 provides a rough and scratchy texture that will literally cause discomfort or skin irritation.

Likewise, when the fill material 28 is exposed directly to the outermost layer of the material 20, such as in a single-layer top 14, then the sound of the fill material 28 rubbing against the material 20 is transmitted directly to the material 20. The material 20, such as a fabric, then operates like a speaker broadcasting sound into the ears of a user. This proximity provides a substantial amplification over what such a sound would be when otherwise presented to ear of a user. All these sound generation, amplification, and transmission properties are reduced by the batting 22 construction. Deadening, spacing, mechanical isolation, and the like reduce generation propagation, and proximity of sound to a user.

A third function of the batting 32 is to provide the texturing, when used in combination with the texture seams 22, applied to make the cells 26 in the material 20. By providing two layers in the material 20, with an intervening layer of batting 32, the seams 22 create a series of concavities 34. Those concavities are found to provide additional stability or resistance to movement when entered by the fill material 28, such as buckwheat hulls.

For example, a combination of concavity 34 to receive certain amounts of the material 28 filling the pillow 10 results in a resistance to flow. Accordingly, a container of the fill material 28 being discrete modules or pieces of material, such as buckwheat hulls, may be poured when not compressed. Nevertheless, the hulls interlock with each other and the concavities 34 pressured against the bottom 16 of the pillow 10, or when the top 14 is pressed against the fill material 28. The concavities 34 receive a certain amount of the fill material 28, and resist its motion along the surface thereon. Thus, like furrows, the concavities 34 at the edges of each of the cells 26 provide a resistance to flow, thus further maintaining the fill material 28 where it is placed by a user.

As the fill material 28 may attempt to slide with respect to the cells 26 or the material 20 forming the cells 26, the concavities 34 crossing its path limit that motion mechanically. The top 14 of the pillow 10, partially filled with the fill material 28, such as hulls 28, will likewise be placed against the fill material 28 under the pressure and movement of a portion of the body, such as the head or neck. As the material 20 or the cells 26 formed in the material 20 are pressed against the fill material 28, then any force along 40 or in a direction 40 substantially parallel to the material 20 results in the same effect on the hulls 28 or other fill material 28 being trapped within the concavities 34 formed by adjacent cells 26. Thus, the movement along 40 or in the direction parallel of 40 to the surface of the material 20 tends to capture the hulls and resist the sliding motion, above the friction that would exist between the material 20 itself and the fill material 28.

Thus, in one embodiment in accordance with the invention portions of the shell of the pillow 10, including the frame 12, the top 14, and the bottom 16, may be formed of a material 20 formed into cells 26. Cells 26 may provide concavities 36 at texture seams 22 trapping the flutes of hulls/and securing a batting 32 between multiple layers of fabric forming the material 20.

In general, as sound 36 propagates in an outward direction 38, it must be propagated as vibration through air, directly from the hulls. Hulls have a substantially different frequency of vibration than does the material 20. The material 20 may typically be formed of a woven fabric. The hulls are substantially a solid, high-frequency resonant material.

Thus, the batting 32 can be very effective, and has been found very effective, in isolating the frequency of motion or frequency of sound generation in the fill material 28. Batting 32 has been found to likewise isolate the generation of sound by rubbing of the fill material 28 against the material 20, effectively reducing sound generation and damping sound propagation. Thus, the pillow 10 operates much more quietly as a result of the constructions of the cells 26, the batting 32, and the resulting mechanical isolation. Accordingly, sound 36 or a sound wave 36 originating from the fill material 28 must pass through intervening air.

This mechanical isolation provided by having multiple layers of the material 20, and an intervening layer of batting 32 provides both space and mechanical isolation. Isolation to reduces the amount of sound 36 generated by the fill material 28 rubbing against the material 20. Isolation also reduces sound from propagating from the fill material 28, into the material 20. It thus limits any response to hulls scratching the material 20 causing it to act as a speaker diaphragm.

A user may tap or pat the top 14, the bottom 16, or the frame 12 in a direction downward 44, upward 42, or a direction along 40 the fabric 20. In general uncompressed granular fill 28 may be urged or shaken laterally, uncompressed transversely, at 90° or at any other angle with respect to the up 42 and down direction 44. The force of tapping or patting may typically have the effect of redistributing the fill material 28, such as hulls 28. The result of tapping down 44 on a portion of the fill material 28 with the flat of a hand, the edge of a hand, a fist, or the like, is to apply a force tending to move the hulls 28 or other fill material 28 away from the point of impact. Thus, a user may form a hollow in the top 14 or any of the particular sides (e.g., panels, portions) of the frame 12. This results in a change of shape to accommodate a desire for a relief region (e.g., indentation) lacking fill material 28 or an adjacent buildup of a support region requiring fill material 28.

Near the frame 12 of the pillow 10, the direction 40 along or substantially parallel 40 to the surface of the material 20 has a similar but more pronounced effect. The barriers 30 operate to further restrict movement of granular fill material 28. In the illustrated embodiment it has been found that the presence of the barriers 30 substantially maintains the shape of the frame 12 and top 14 with respect to the bottom 16 of the pillow 10 in use.

In general, it has been found that the barriers 30 tend to resist movement of the fill material 28 in a direction 40 along the material 20 enclosing it. Likewise, it has been found that the concavities 34 formed in the material 20 by virtue of the texture seams 22 also tend to add a degree of resistance to movement of the fill material 28 along the surface of the material 20. As a practical matter, the particulate nature of the fill material 28 renders it less likely that the fill material 28 can bridge the concavities 34 to slide with respect to the material 20. Such sliding and bridging would be the case with batting or other conventional fill materials.

Referring to FIG. 11, notwithstanding the comparative stabilizing influence of the barriers 30, the wall portion 12 or the frame 12 of the pillow 10 may be caused to extend in a more-or-less circular cross-sectional configuration, rather than in a straight line. For example, when suspended as illustrated in FIG. 11, the pillow 10 may typically be only half filled with the fill material 28. This percentage or fraction of fill experienced by the pillow 10 is selectable by a user.

In a typical embodiment, the fill material 28 flow and adjustment benefits from having additional space into which it may flow. A particle of a granular fill material 28 will readily fall under the unmitigated influence of gravity. However, once the pillow 10 is laid on the bottom surface 16, the tendency of granules of buckwheat hulls to move laterally is substantially decreased. For example, in free fall, the particulate material 28 used as fill material 28 effectively can free fall to the lowest permissible point.

However, other designed forces within the material 20 of the frame 12 top 14, and bottom 16 will tend to operate together to contain the "pressure" represented by the weight of a user on the quantity of the fill material 28 enclosed therewithin. Once the pillow 10 is laid on the bottom 16, in the orientation of FIG. 10, the particles of the fill material 28 are no longer in free fall. Instead, each contains extensions or flutes projecting in three directions that tend to engage the corresponding flutes or extensions of other particles. Accordingly, a certain stability exists due to the interaction between the particles and requires a threshold force to displace particles.

An individual may add energy by tapping, patting, hitting, punching, or otherwise shifting the particles of the fill material 28 about the interior volume of the pillow 10. Nevertheless, under the influence of gravity, a limited and comparatively stable distribution of the particles of the fill material 28 occurs upon laying the pillow down on a supporting surface. Thus, a supporting surface onto which the bottom 16 of the pillow 10 is placed will support the pillow 10 with a force 44 or an upward direction 42.

Meanwhile, the individual particles of the fill material 28 will exert a force downward 44 or a downward 44 force against the bottom 16, and against one another as well. Movement and a lateral force in a direction 46 in response to forces in the upward 42 and downward 44 directions is resisted to a certain extent by the interaction between the extensions on the particles of the fill material 28.

Upon application by a user of a downward force 44 against the top 14 of the pillow 10, two principal influences exist. To a certain extent, the extensions, on the particles of the fill material 28 tend to interlock and resist lateral movement in response to force in the downward direction 44. By the same token, application of more pressure or force, particularly if applied by repeatedly striking, may provide dislodgement of the particles with respect to one another. This permits a redistribution of the fill material 28. Thus, in a pillow 10 in accordance with the invention, a degree of control over distribution of the fill material 28 may be substantial.

An additional benefit to a pillow 10 in accordance with the present invention is the availability of the fill material 28 to refill and support the fill material 28 under and around the supported bodily members of a user. For example, conventional pillows tend to have substantially conical corners tapering to a very small point. These corners have been found to present two problems when used with the granular fill material 28.

One problem is simply the volume. Such corners contain about one third the volume or less compared to a parallel-epiped of equivalent maximum dimensions. Accordingly, much less fill material is contained. With the corner holding so little volume of an equivalent rectangular shape, any loss of the fill material 28 near a bodily member of the user cannot be readily refilled from the corners nearby.

Also, the corners tend to interfere with the shoulders of a user. That is, in a sleeping position, the shoulders are near the head, with the neck connecting. In order to obtain effective placement of the pillow 10 supporting the neck from the shoulders to the head, the corners of the pillow 10 typically interfere with the shoulders of a user. This causes the shoulders to push against the corners of a conventional pillow, either moving it away or removing or compressing much of the fill 28 that would otherwise be in the corners. Inasmuch as the corners come to points, any impact on the corner may typically dramatically influence the amount of fill near the corner.

By contrast, in a pillow in accordance with the invention, the frame 12 or wall 12 contains a large amount of fill near the corners of the rectangular, or substantially rectangular, top 14 and bottom 16. This provides space for displaced fill material 28 to move, upon impingement by a shoulder of a user. Thus, the extensive height of the frame 12 provides place for displacement of the fill material 28. Accordingly, the fill material need not leave nor flow away from a bodily member of the user, but may rearrange about the displaced portion of the frame 12. Moreover, the pillow 10 need not be under the shoulders in order to be under the base of the neck. Neither will residual resilience in the pillow 10 push it longitudinally away from the shoulders, leaving the neck unsupported.

Continuing to refer to FIG. 11, specifically, while likewise continuing to refer generally to FIGS. 1 through 43, the pillow 10 may be prepared for rest by simply grasping one portion of the frame 12. Lifting permits the top 14 and bottom 16 to drop vertically therefrom, containing the opposite portion of the frame 12 therebetween. Inasmuch as the granules of the fill material 28 are in free fall, it is a rather simple matter to shake the pillow 10, to completely fill the region about the barriers 30 at the seams 24 between the frame 12 the top 14, and bottom 16.

Figure 12:
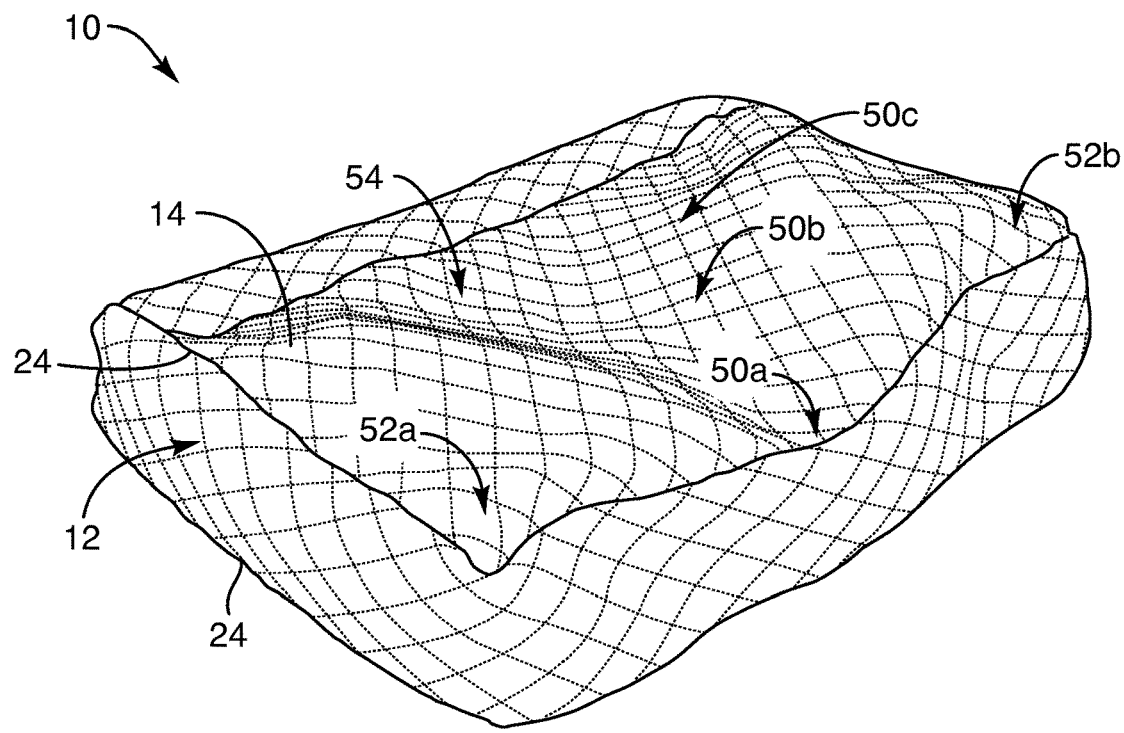
FIG. 12 is a perspective view of the apparatus of FIG. 1 in use as adjusted for a back-sleeping configuration.

Referring to FIGS. 12 through 20, and particularly the embodiment of FIG. 12, the indented regions 50 may be indented by patting, tapping, or by movement of a bodily member resting on the pillow 10. For example, the indented region 50a may be formed about the neck of the user. In accordance with certain aspects of the invention, the indented region 50a may extend from near the shoulders, to the base of the skull. Accordingly, more support is provided to the lower end of the skull by supporting the neck. Likewise, the shoulders may indent the wall 12 on either side of the indented region 50, thus permitting the indented region 50a to support the entire extent of the neck.

Meanwhile, the region 50b may extend as a fan shape, particularly as the skull or cranium may move from side to side during natural sleep, or prior to sleep. Accordingly, the indented region 50b may actually extend down 44 below the region 50a supporting the neck. If desired by a user, the region 50b may be slightly higher.

However, the back of the skull actually extends behind the neck, or under the neck in a sleeping configuration. By contrast to an incline or sitting position, wherein the head may be canted forward in sleep, the head will lie back, the neck requiring support by the indented region 50a. Supporting the neck will require support at a location that will typically be higher than that of the back of the skull in the indented region 50b.

Meanwhile, the regions 52a, 52b are filled regions containing a substantial amount of the fill material 28 by virtue of the large cross-sectional areas and resulting large volumes. Accordingly, the regions 52a, 52b resist evacuation, or further evacuation, of the indented region 50a by receiving amounts of the fill material 28 pushed away from the indented region 50a, but then returning it if opportunity provides.

The substantial volumes in the regions 52a, 52b thus can compensate against excessive migration of fill material, with resulting resistance to further flatting of the pillow 10 during sleep. This has been found to be a substantial benefit over prior solutions, even those that rely on granular fill materials.

For example, certain devices may attempt to restrict fill by closing down portions of the proposed apparatus in order to limit the escape of fill materials. Nevertheless, such embodiments suffer from hardness, discomfort, and still lose fill from thin conical corner portions having such substantially reduced volume. Compared to the present invention, such concepts also suffer from the fact that the corners are at a low point, and are not positioned above an indentation 50a 44, to drop fill downward back into the areas around the bodily member to provide support.

Moreover, it has been found that the movement of the head of a user in a twisting or rotational motion about the axis of the neck, or in swinging side-to-side on the shoulders tends to migrate fill material 28 from the indented regions 50b, 50c back into the regions 52a, 52b. Thus, by having the volumetric capacity to receive the fill material 28 into the regions 52a, 52b, a pillow 10 in accordance with the invention maintains the desired distribution of fill desirable to support the comfort of a user.

The partially filled region 54 may include some material driven into the region 54 by manipulation of the pillow 10 by a user. Tapping, patting, punching, or otherwise dislodging the granular fill material 28 within the pillow 10, a user may provide any desired amount of fill, in the region 54. The amount of fill may vary from total evacuation to a substantial fill amount.

It has been found effective that the pillow 10 in one embodiment have a wall 12 or frame 12 that extends approximately one to six inches, and typically about four inches between the structural seams 24. Meanwhile, a width of from 8 to about 18 inches and typically about 15 inches, with a length of from about 12 to about 30 inches (typically about 18 inches) provides suitable expanse for the normal motion of sleep. Meanwhile, filling about half such a volume in fill material 28 provides suitable adjustability with a suitable amount of fill for most users. Nevertheless, a user may provide any amount of fill 28 desired by opening the closure 18 and adding the fill material 28 therethrough.

Figure 13:
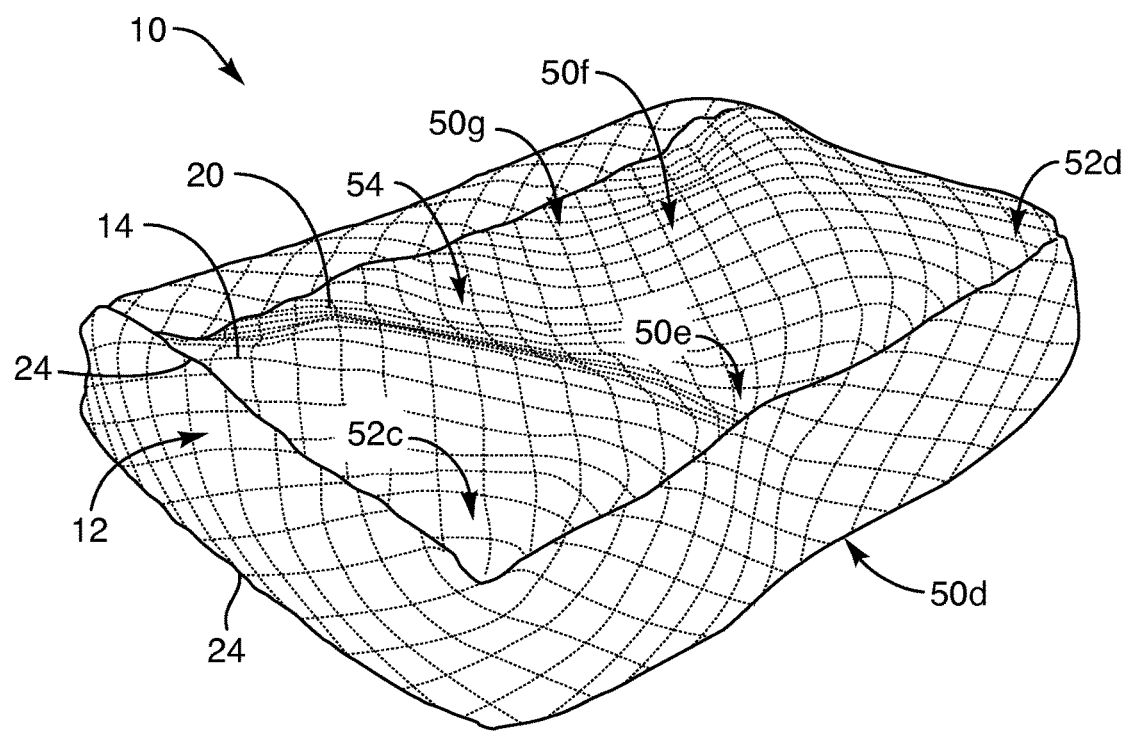
FIG. 13 is a perspective view of the apparatus of FIGS. 1-2 arranged in a partially-filled configuration as adjusted to implement side-sleeping support.

In the embodiment of FIG. 13, the shoulder of a user sleeping on is or her side may form a relief or cavity in the indented area 50d, while the neck, immediately proximate the shoulder, may rest on the indented area 50e. Ultimately, as the head connects to the neck near the indented region 50f, the level of the fill material 28 may decrease in accordance with the additional width of the skull as compare to that of the neck.

Likewise, the region 50g may be at a level commensurate with that of the region 50f, supporting the maximum width of the skull. Accordingly, in certain embodiments, the region 50g may be substantially lower than the indented region 50e with the region 50f supporting the cheek, jaw, or other portions of the head of a user, having less dimensional width than the widest part of the skull resting on the area 50g.

Meanwhile, the corner regions 52c, 52d provide the large volume of material 28 maintained from the initial fill and from displacement of material out of the regions 50e, 50f, 50g. The fill 28 therein is available to support against migration (evacuation) and to refill those areas if opportunity affords. Thus, the motion of the head of a user about the regions 50f, 50g tends to roll or push a certain amount of the granular fill material 28 back into the corners 52c, 52d, thus maintaining the surrounding support for the regions 50e, 50f, 50g.

Moreover, in the illustrated embodiment, a side-sleeping person may find the additional benefit of the regions 52c, 52d as the head may be moved from a direct extension from the shoulders, to a forward inclination or backward inclination with respect to the shoulders. In response to pressure and repeated movement the fill material 28 may provide additional impressions to support, yet relieve pressure on the head and neck of a user, by providing spatial displacement.

Another benefit of the embodiment of FIGS. 12-13 is the relief afforded with the user of a CPAP mask. A user has but to move back and forth, displacing fill 28 to provide relief for such a mask. Such movement, by jostling the fill material 28, provides a redistribution thereof forming relief, an indentation 50 or pocket 50, for the mask to occupy. Upon displacement, the fill material 28 lacks the ability to provide the constant, resilient, spring-like pressure back that would exist in a conventional pillow.

For example, in a conventional pillow, the materials operate according to the typical spring constant equation, or Hooke's law, wherein force is equal to displacement times a constant. In a conventional pillow, displacement controlling the force is extremely important. It often causes pressure points because due to mismatched surface areas, discontinuities in matching the human profile supported, and pre-loading forces applied before certain areas of the pillow have deflected to contact and support the corresponding portion of a bodily member.

For example, if a comparatively thin region or small thickness exists, as it does near the edge of a conventional pillow, then the total force obtainable is a correspondingly small function reflecting the displacement thereof. Meanwhile, near the center of the pillow where the bulk of the material exists, displacement through a particular distance reaches a much higher maximum value. Thus, the shoulders and neck of a user are found comparatively unsupported.

For instance, because the displacement required by the head in displacing the fill material of the center of a pillow translates through a great distance. The resisting force becomes very much higher due to the greater displacement of the larger thickness of the center of the pillow. Also, the force increases with the additional displacement that the projecting back of the head demands in order to have a hollow shape in which to rest. Near the edge, by contrast, the neck of a user is often virtually completely unsupported.

Thus, in an apparatus 10 or pillow 10 in accordance with the invention, displacement may take place independent from the spring constant of the fill 28, and without changing the spring constant or creating a bias or pre-load on a user. Meanwhile, once the fill material 28 has been stabilized, then its natural spring constant or resilience can act to provide a distributed pressure or force to support at all desired locations. Each area receives approximately the same effective spring constant and available displacement. Therefore, each has about the same pressure presented to the bodily member of a user. By contrast, conventional pillows cause a lack of support for the neck near the edge and an uncomfortable pre-load lifting the head of a user at an uncomfortable angle at the center of the pillow.

Referring to FIG. 13, then, a shoulder of a user impinging on the region 50d or the indented region 50d provides additional advantages. Unlike a conventional pillow, the fill material may be adjusted to be thickest instead of thinnest nearest the edge of the pillow. Meanwhile, the amount of material is completely selectable anywhere, removing the force "pre-load" otherwise typical near the center of a conventional pillow.

Accordingly, the neck and shoulders of a user are exposed to their own customized profiles, providing the thickness and pressure needed. They are not abandoned to a lack of support from the least displacement and pressure possible as in most pillows. Since force or pressure is directly proportional to the amount of the displacement of any Hookian fill material, then the shape of the back of the skull or the side of the skull, compresses an area that presents no pre-load. Each area is filled to a greater extent, or lesser extent as needed, and thereafter provides support.

Therefore, the net force or pressure on the head is substantially no greater nor less than that on the neck weight of a member being distributed over its profile, and all remain properly supported. The indented regions 50 provide a particular uncoupling of the initial displacement from subsequent supporting pressure.

When considering displacement of a pillow, the head of a user is wider, typically, than the neck. When lying on one's back, the depression in a conventional pillow, caused by the skull, is substantially greater than the deflection caused by the neck. As the portion of the pillow near the edge is particularly thin, the total displacement under the neck is considerably less than that near the thicker central portion of the pillow, where lies the head. Not only does the head profile need to be at a greater distance (perpendicular to the neck), but must displace fill to that extent at the thickest part of the pillow. The neck rests at the edge on much less material. Thus, the resulting pressure on the head is substantially greater than that provided on the neck, if contact is made at all. Thus, it is not uncommon for a sleeping user to obtain substantially no effective neck support.

By contrast, in a pillow 10 in accordance with the invention, the supporting force due to the resilience of the fill material 28 is uncoupled from the initial displacement. Rather than the entire displacement being a compressed, resisted, spring-loaded displacement, the initial displacement remains free of residual force. Therefore, the net pressure on the neck, face, skull and so forth of a user is a result only of compression by virtue of the weight of the bodily member supported. Its displacement provides the only elastic deflection of the fill material 28. Thus, the pre-load or biasing pressure that would otherwise exist is uncoupled, and is not present.

Accordingly, whether sleeping on the back, as in the configuration of FIG. 12, or sleeping on the side, in the configuration of FIG. 13, every bodily member from the shoulder, to the lower neck, to the central and upper neck, to the face, to the skull may all be nested into the pillow 10, to create an initial displacement having minimal residual or bias force. In fact, the residual force due to initial displacement of the fill material 28 should be substantially zero.

Likewise, displacement may occur in any direction. For example, if the relief 50d or the indented region 50d of FIG. 13 were made in any conventional pillow, then the resulting force due to the spring-like forces of the fill material would tend to displace the pillow away from the shoulder of a user. That is, all displacements thereof result in residual forces.

By contrast, the indented region 50d may be formed, leaving substantially no residual force, and therefore leaving the pillow 10 properly located, and permanently located as desired by a user. Thus, a bodily member need not be exposed to any substantial biasing force or pressure in order to maintain its desired position. Likewise, no localization of residual force exists by virtue of maintaining position against such a bias force. Support exists only in response to the weight of a bodily member fitted and supported by the fill material 28 in the pillow 10. An increase in localized pressure will result in shifting fill material 28 away therefrom, once some threshold is reached to disengage the flutes of the fill material 28.

Figure 14:
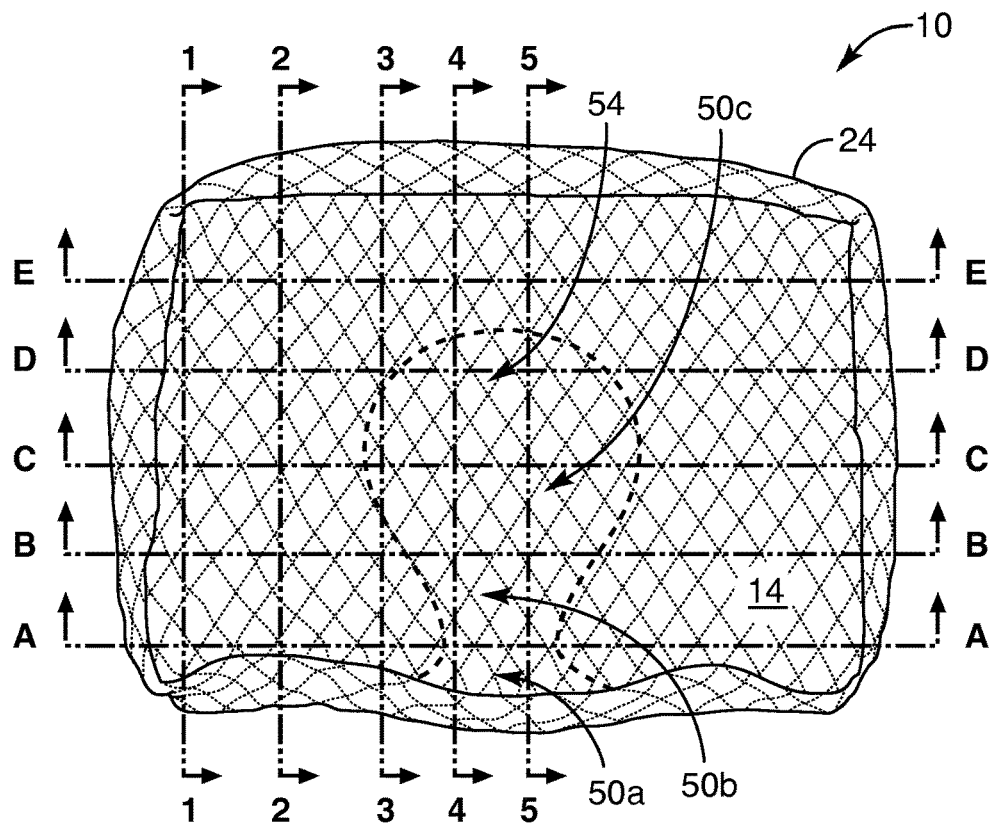
FIG. 14 is a top plan view of the apparatus of FIG. 12.
Figure 15:
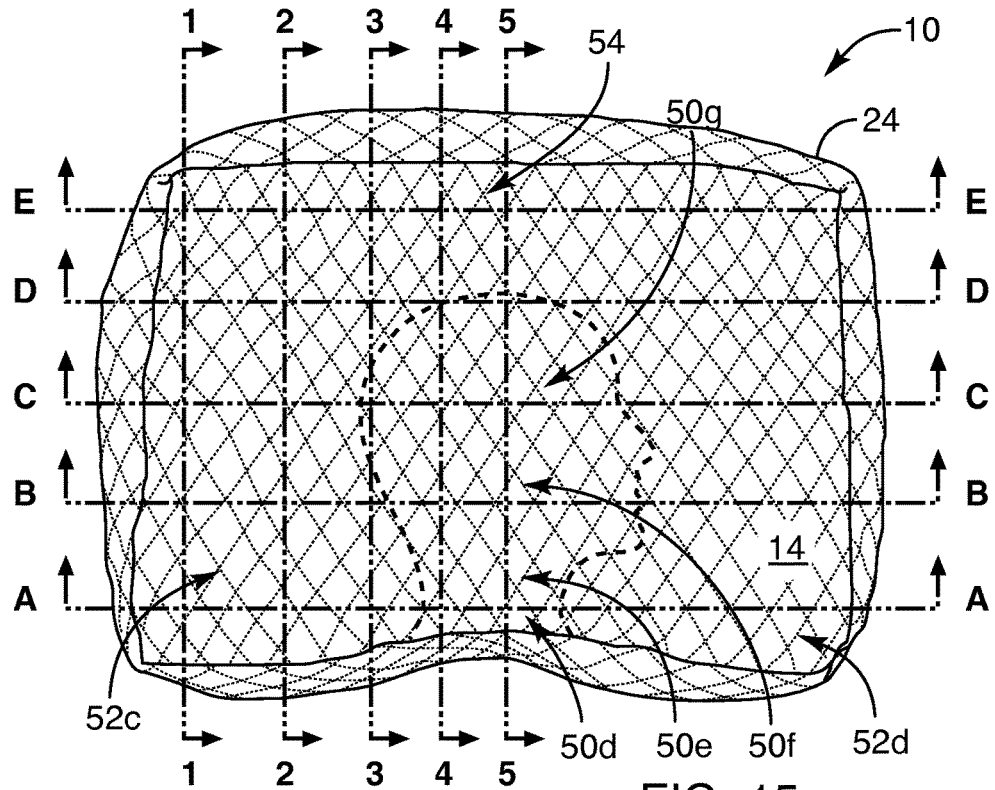
FIG. 15 is a top plan view of the apparatus of FIG. 13, that is, arranged in the sleeping configuration for side sleeping as in FIG. 13.
Figure 16:
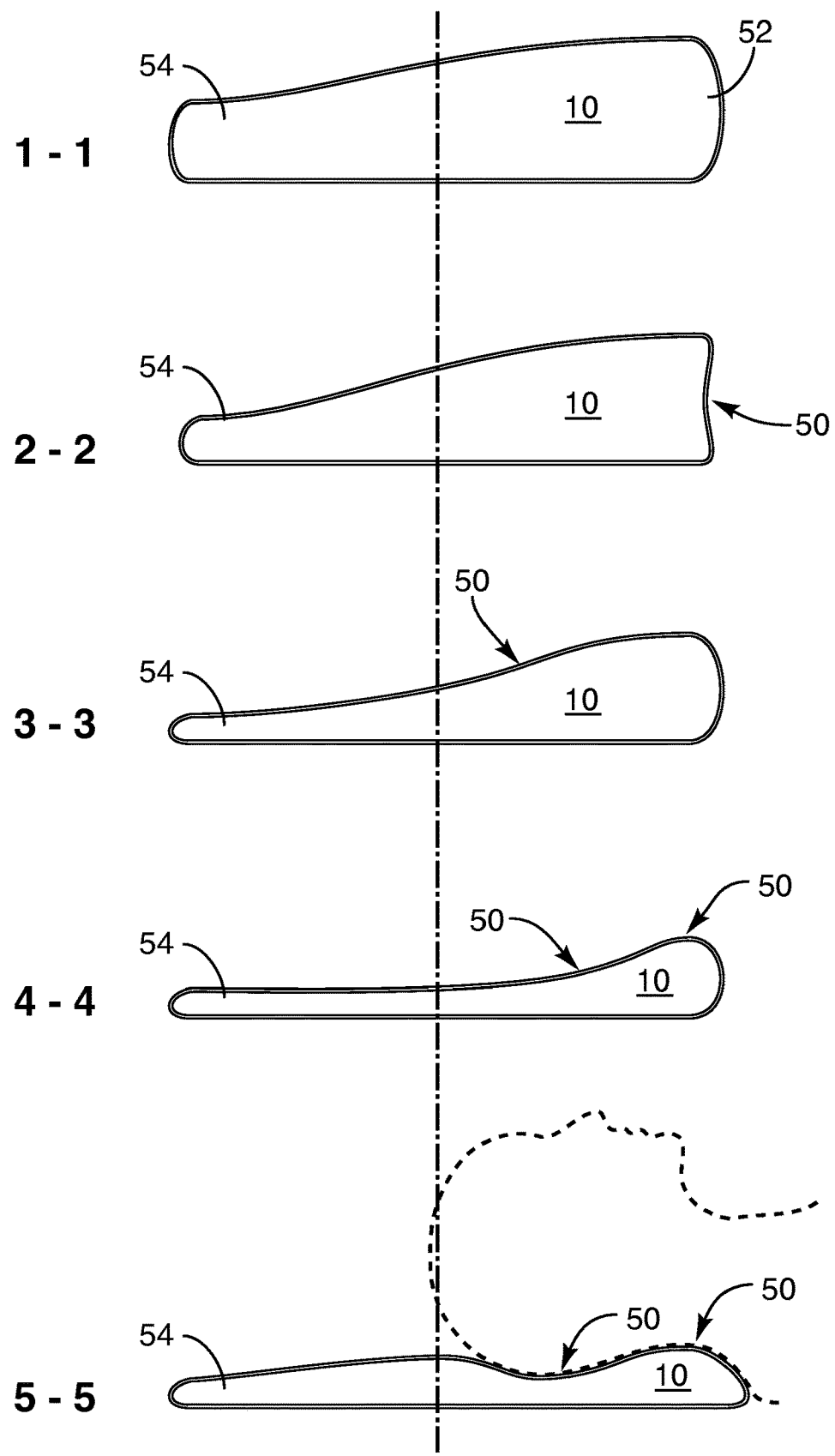
FIG. 16 is a series of end cross-sectional views of the apparatus of FIGS. 12 and 14.
Figure 17:
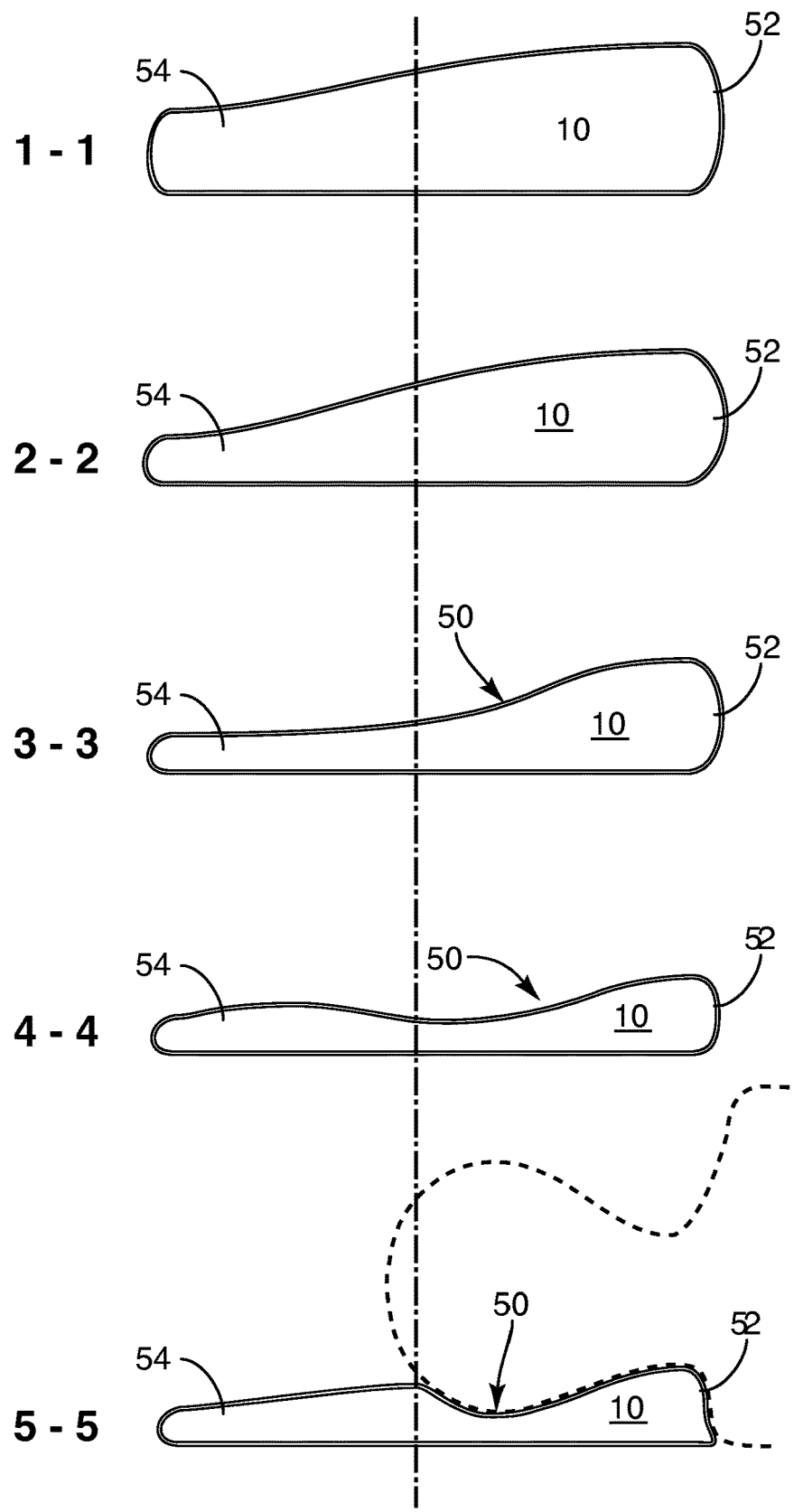
FIG. 17 is a sequence of end cross-sectional views of the apparatus of FIG. 1 as arranged and configured in the arrangement of FIGS. 13 and 15.
Figure 18:
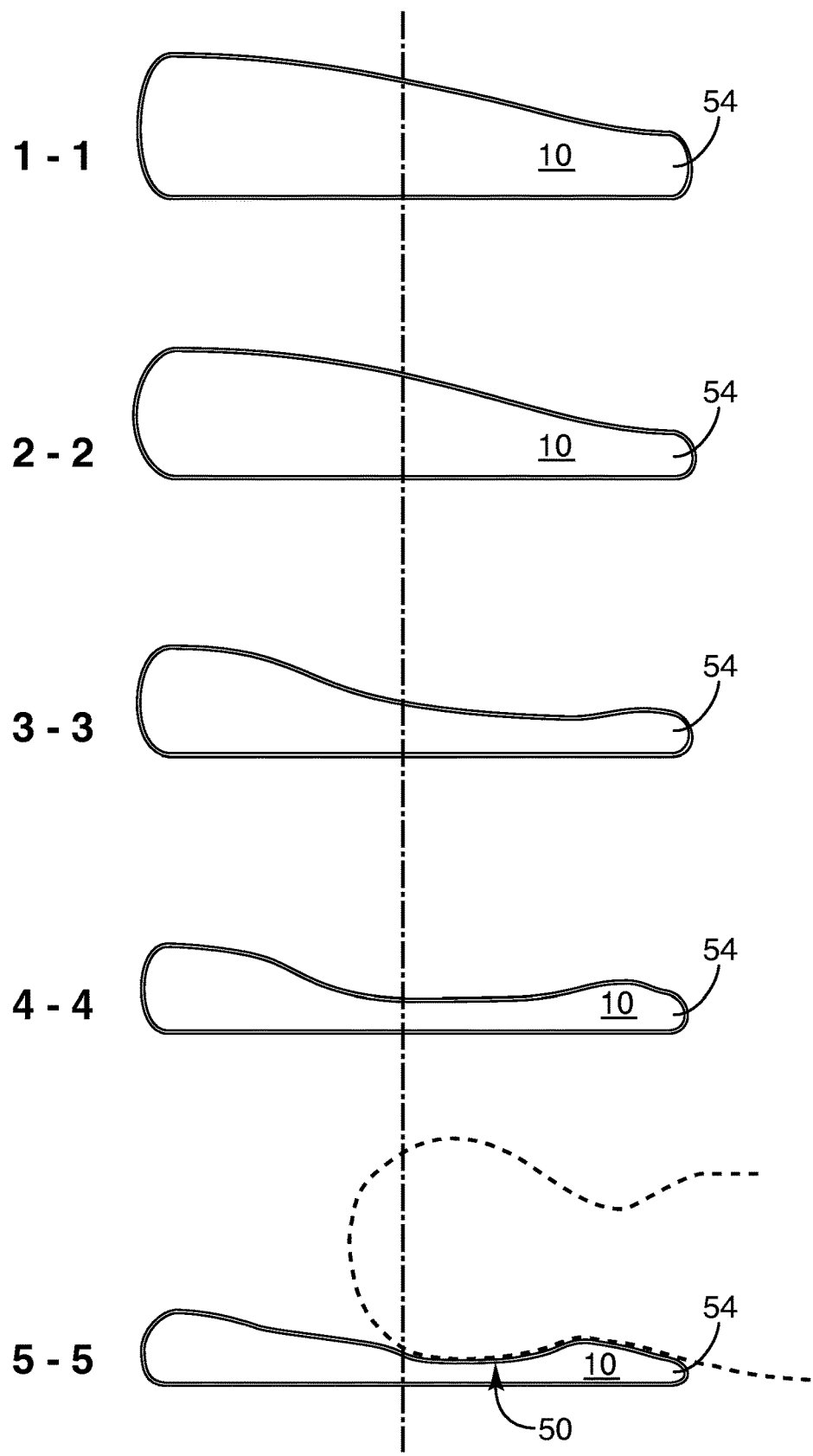
FIG. 18 is a series of end cross-sectional views of the apparatus of FIG. 1 arranged for a stomach-sleeping arrangement.

Referring to FIGS. 14 and 15, the top plain views of the configurations of FIGS. 12 and 13, respectively are marked with numbers 1-5 as well as with letters A-E. Thus, these plain views identify location of certain cross sections that will be taken. In FIG. 16, the end view cross sections at sections 1-1 through section 5-5 are illustrated. Similarly, in FIG. 17, the end cross sectional views of the embodiment or configuration of FIG. 13, as illustrated in a plain view in FIG. 15 are illustrated. Similarly, FIG. 18 illustrates the end cross sectional views of the pillow 10 when configured for a stomach-sleeping mode.

Figure 19:
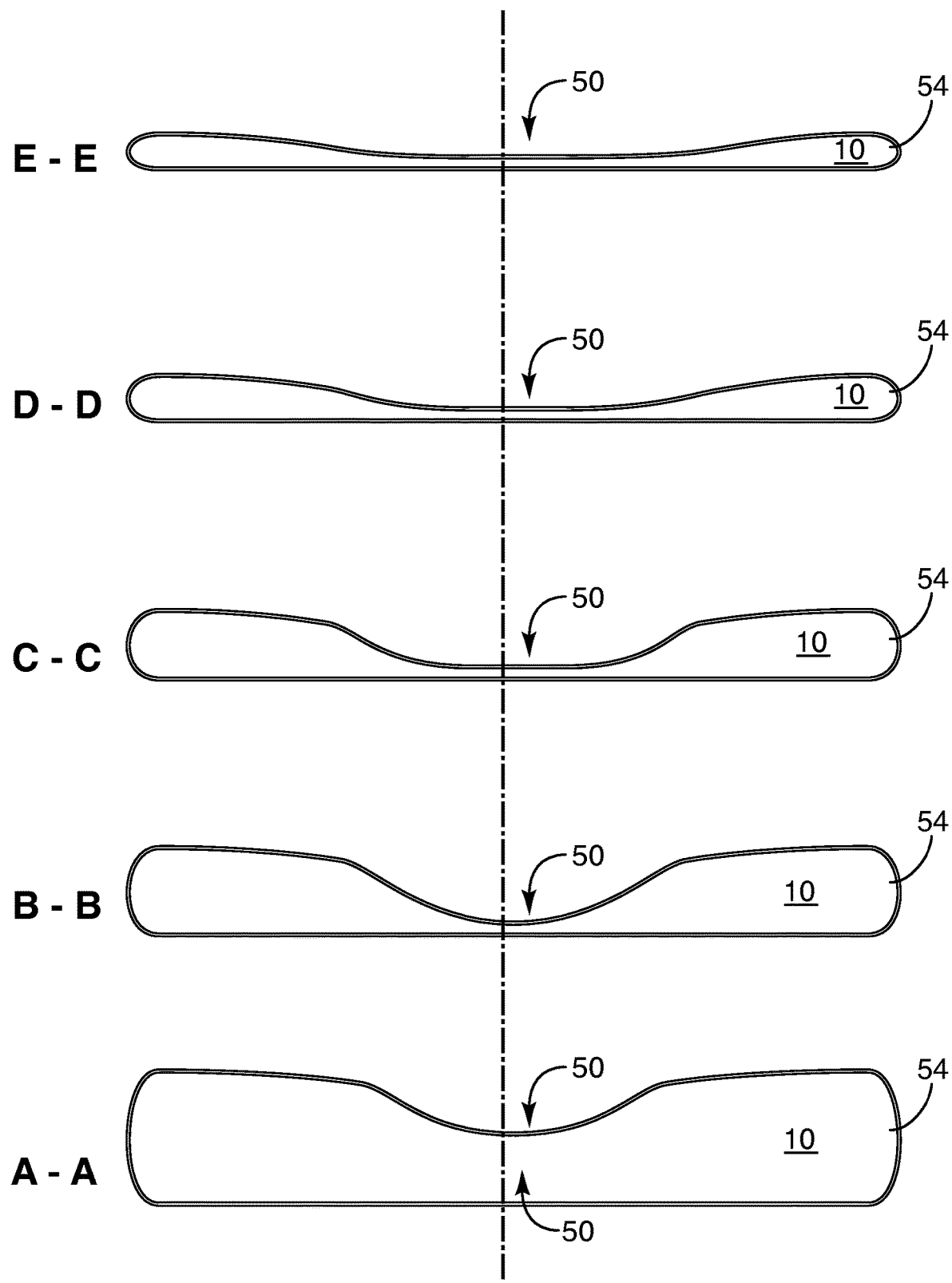
FIG. 19 is a series of side cross-sectional views of the arrangement of FIGS. 13, 15, and 17.
Figure 20:
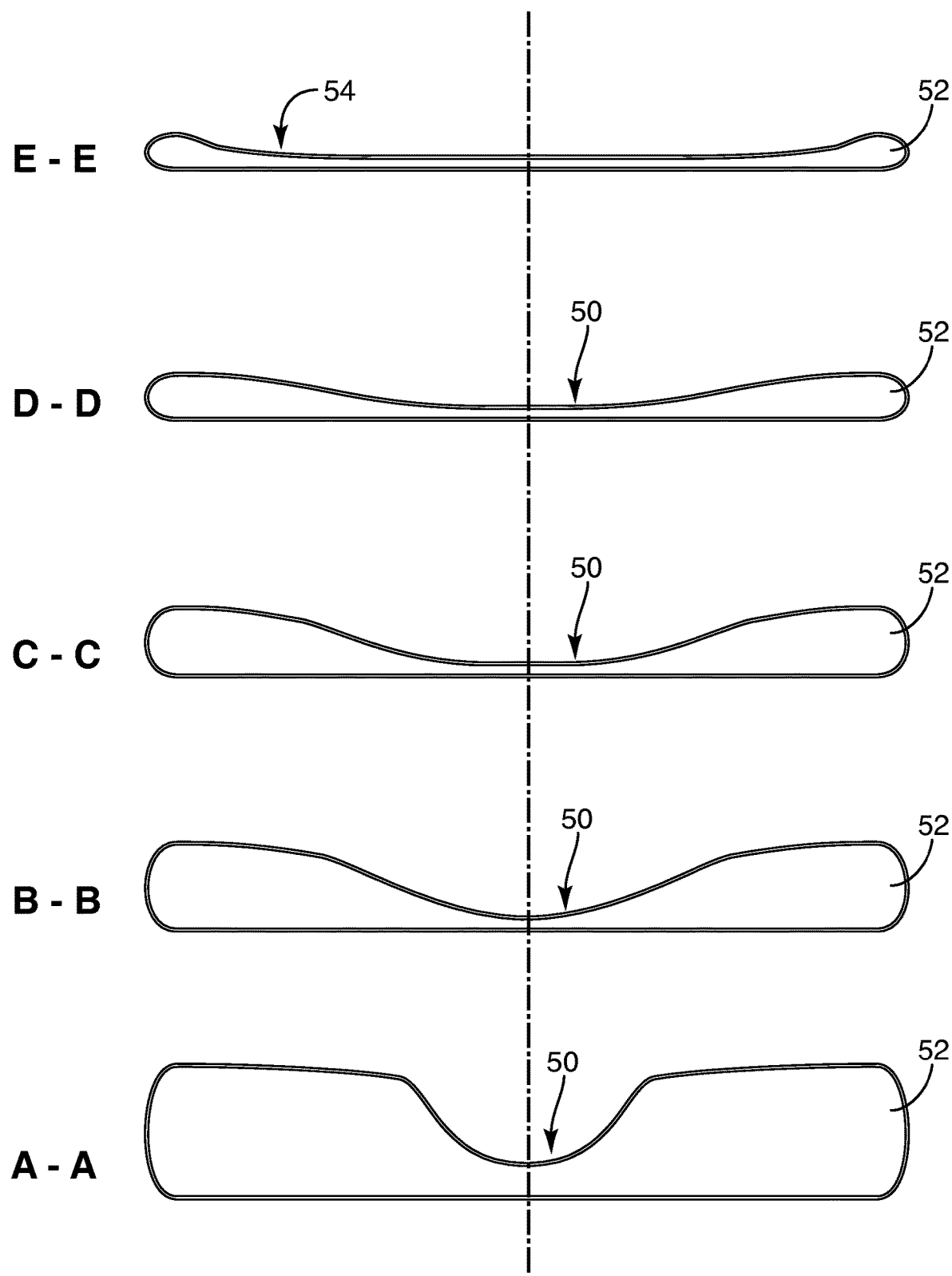
FIG. 20 is a series of side cross-sectional views of the arrangement of FIGS. 12, 14, and 16.

FIG. 19 illustrates the embodiment or configuration of FIG. 13 from a side elevation cross section taken at sections A-A up through sections E-E. Similarly, FIG. 20 shows the side cross sectional views of sections A-A through sections E-E in the back-sleeping configuration of FIGS. 12 and 14.

As can be seen, the pillow 10 in accordance with the invention has several advantages. By providing the large regions 52a, 52b acting as reservoirs of the granular fill material 28, the stability of the indented regions 50 may be maintained. Meanwhile, any migration out of the regions 50 will tend to replace a certain amount of the material in the regions 52a, 52b.

Similarly, any opportunity to move material out of the regions 52a, 52b will result in a downhill movement of the fill material 28 typically to one of the other indented regions 50, all of which begin at a lower elevation. Thus, the pillow 10 tends to be substantially more stable than prior solutions, even those that may rely on granular fill.

One may note that in the embodiments of FIGS. 12 and 13, the head of a user may move in an arc anchored by the neck at the shoulders. Accordingly, the broad indented expanses 50c and 50g may tend to actually drive fill material back towards the regions 52a, 52b and 52c, 52d when motion results in net movement of the fill material out of the regions 50c, 50g, respectively. Thus, bodily motion and the readjustment or tossing that an individual may do in sleep tends rather to maintain the shape of the sleeping surfaces or indented regions 50, rather than destroying them.

The locations of the corner areas 52a, 52b, 52c, 52d tending to pick up the sweep of the fan shaped regions 50c, 50g, respectively, tend to maintain, rather than deplete the large regions 52. By the same token, the very volume capacity of the regions 52 tends to minimize any depletion of a particular indented area 50 by providing an overwhelming volume of the fill material 28, and that at a higher elevation, which can be flowed downward with additional motion or movement by a bodily member on the pillow 10.

Figure 21:
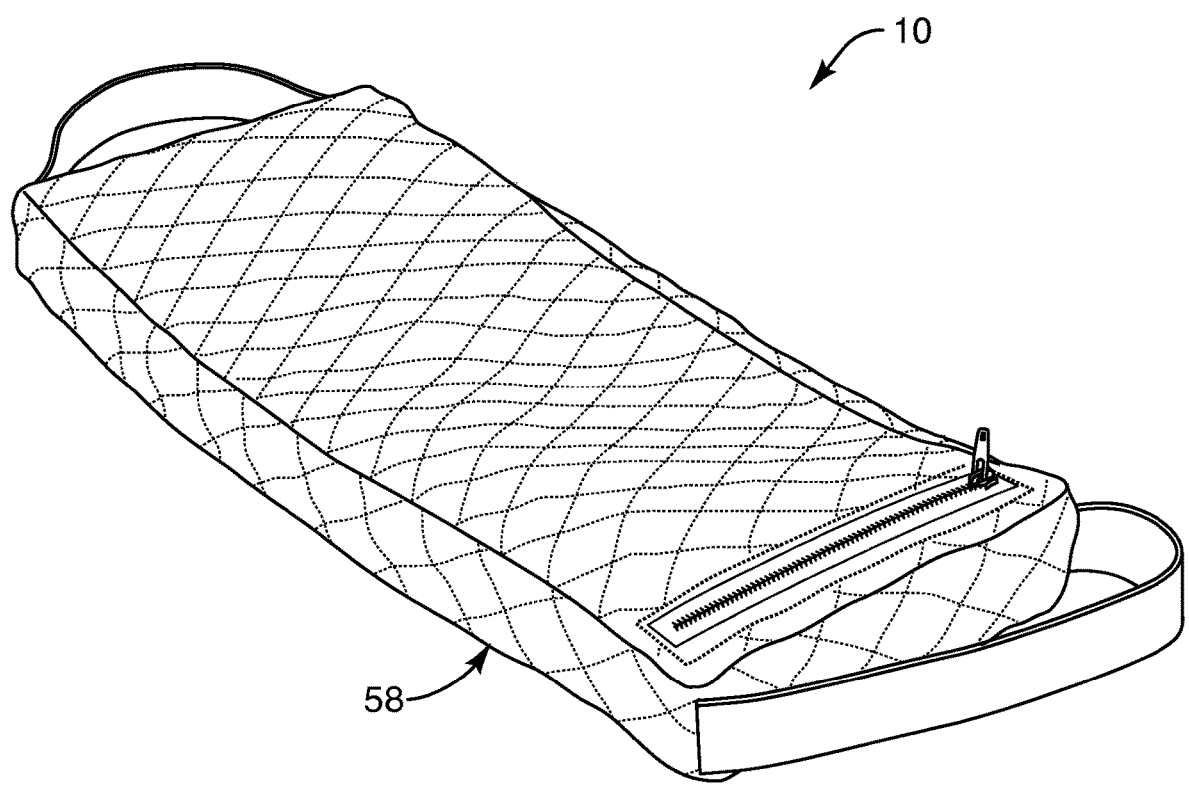
FIG. 21 is a perspective view of one alternative embodiment of an accessory for use in accordance with the invention arranged for lumbar support use.

Referring to FIG. 21, in one embodiment of an apparatus 10 and system in accordance with the invention, an additional pillow may be provided. This pillow 58 may provide particular augmentation. The spine of a human is not distributed along a straight line. Just as the neck requires support, in order to maintain its shape with respect to the shoulders and skull, the lumbar region of the back may need additional support in order to maintain its curvature with respect to the trunk and torso of a user.

In one embodiment of a method and apparatus in accordance with the invention, a lumbar pillow may be place under the lower back of a user in order to provide the proper curvature of the spine. By containing a similar material 20 filled partially by a fill material 28 as with the head pillow 10, a lumbar pillow 58 may provide for further proper alignment of a spine of a user.

In the illustrated embodiment, the lumbar pillow 58 may be configured to primarily support a vertical load, or a load acting in a vertical direction 44. Accordingly, a user may nestle against the lumbar pillow 58 in order to provide displacement or relief locations 50, pockets reduced in, or devoid of, fill material 28 to accommodate the particular shape of a user's back.

The particular size, as well as the vertical walls of the lumber pillow 58 may provide a certain containment, in order to restrict the net flow of the fill material 28 to behave substantially like a thixotropic (i.e., no movement in response to less than a threshold force) or similar material. That is, the fill material 28 can flow, but its containment within the overall outer container limits its ability to leave. Accordingly, the net amount of the material will tend to distribute itself within the walls, much as a liquid would configure itself, as if the user were sleeping on a liquid filled lumbar pillow 58. However, since the uncoupling of the initial displacement from the net supporting displacement exists in this lumbar pillow 58, a substantially even pressure may exist, while still providing a substantial vertical pressure support at a substantially equal value throughout.

Figure 22:
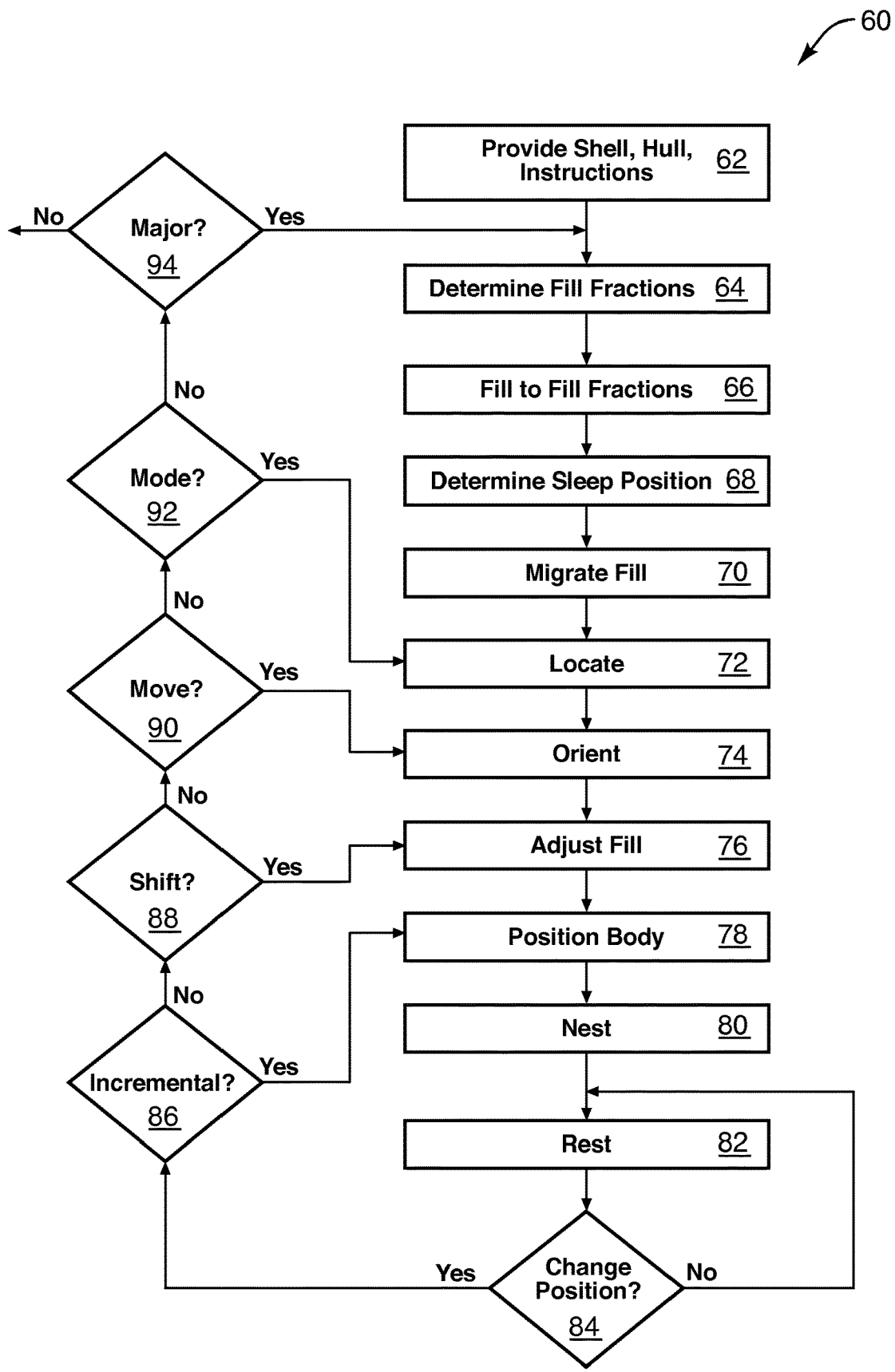
FIG. 22 is a schematic block diagram of a process for making and using an apparatus in accordance with FIGS. 1-21.

Referring to FIG. 22, a method 60 in accordance with the invention or system 60 may involve providing 62 a shell, as well as a fill material 58. The shell may include a frame 12 sewn to a top 14 and a bottom 16. Accordingly, some amount of discretized, self-engaging granules of a fill material 28, such as buckwheat hulls may be provided 62 along with instructions to a user.

Thereafter, the user may determine 64 a fill fraction. For example, an individual may determine the amount of fill desired. Thereupon, the user may fill 66 the pillow 10 with the desired amount of fill material 28. This process of filling 66 may be repeated several times as a user tries initially to find a suitable amount. Filling 66 may involve opening the closure device 18, pouring in a quantity of the granular fill material 28, sealing the closure 18 and then laying the pillow 10 flat on a supporting surface.

A user may next determine 68 a sleep position. Different people use pillows for different purposes. Some individuals may wish to support the head and neck in a back-sleeping position. Others may wish to support the head and neck away from the shoulders in a side-sleeping position. Still others, may desire to support the shoulders in order to permit the head and face to extend downward, in a stomach-sleeping position.

Yet others may desire to support a leg, foot, arm, or the like in an elevated position. Similarly, others may choose to support a leg or knee in a side sleeping position, against the impingement of another bodily member.

For example, mattresses do not always provide the desired displacements. Following various injuries or surgeries, support may be required for a particular bodily member such as an arm or leg. Likewise, an expectant mother may desire to provide stomach support in a side-sleeping position. Accordingly, a user may determine 68 a desired sleeping position.

A user may migrate 70 the fill in order to provide a filled location suitable for forming certain regions 50 having indentations or depressions to receive a bodily member, with support on all sides. One of the benefits of an apparatus 10 in accordance with the invention is that support may effectively cover 180° of a curved surface of a bodily member.

For example, sleeping with the head on a wooden block provides support only at the area of contact, which would be theoretically, a point. For example, if a steel ball were resting on a steel surface, the contact area is minuscule. Of course, bodily tissues will deform to a certain extent. Thus, a user having a wooden block under the head would have a somewhat greater surface area of support than would a steel ball on a steel block. Nevertheless, the force concentration caused by the weight of the head on such a small area may cause local discomfort. Also such a "point load" may cause leverage, adding general discomfort, for a lack of support of the neck.

By contrast, an apparatus 10 in accordance with the invention provides the ability to wrap around or surround the entire lower surface of a member. Typically this will be at least in a region of from about 45° to about 180° of total envelopment support for the underside of a bodily member. Thus, the neck is not supported merely in the center, but from side to side thereon. Moreover, the entire neck, or head, or shoulders, etc. will be supported with substantially the same pressure, or force per unit area dependent only on it's applied weight. This support force or pressure is provided without a disparity in the distribution thereof.

For example, from side to side, and longitudinally along the neck of a user, the pressure of a conventional pillow of any fill type may not support the entire, longitudinal, nor lateral, two-dimensional profile, as does a pillow in accordance with the invention. Moreover, where fill is an elongate material, rather than a granular, movable, flowable material, the pressure applied to a bodily member will be uneven, causing high pressure locations or "pressure points" of discomfort.

By contrast, an apparatus in accordance with the invention may provide support all the way across from side-to-side of, and longitudinally along, the neck and head of a user.

In order to migrate 70 the fill material 28, a user may lift the pillow 10, typically grasping a portion of the frame 12, and permitting the fill material 28 to free fall to the opposite extreme of the frame 12 or wall 12 of the pillow 10. A user may then tilt the pillow 10 to one side, and lay the bottom 16 on a supporting surface, such as a bed.

A user may then permit the mutually engaging material 28 to flow somewhat downward. A user may then tap it, poke it, pat it, punch it, or otherwise move it further by applying forces vertically 42, 44 or in any other direction, such as laterally 46, in order to disengage and move the fill material 28 to a distribution desired. In certain embodiments, a user may simply tap with a finger or hand, including an edge or a palm of hand, in order to create desirable indented regions 50. Ultimately, a user may push, pat, poke, shake, or otherwise migrate 70 any desired amount of the fill 28 to a location where desired.

Typically, comparatively massive migrations of the fill material 28 may be imposed by simply grabbing any portion of the pillow, shaking it. Permitting the fill material 28 to free fall to an opposite portion of the pillow 10, thus forms a large bulge region of maximum thickness. That bulge region may then be modified by a user according to a desired shape for sleeping.

A user may next locate 72 the pillow 10 according to the desired use. For example, the user may choose to locate 72 the pillow 10 close to the shoulders, under the neck, under the face, under the back of the skull, or the like.

Likewise, a user may orient 74 the pillow in accordance with the body location. For example, a user may desire to support the side of the stomach for an expectant mother. The pillow 10 may be positioned according to the shape and orientation of the body. Likewise, an individual may choose to orient 74 the pillow 10 in accordance with sleeping position, body part to be supported, or the like. For example, a pillow 10 may be oriented to support the back, the lumbar region, a shoulder, a stomach, head, neck, or face for stomach-sleepers, back-sleepers, side-sleepers, and so forth.

A user may adjust 76 the fill in order to match the impression (e.g. profile) desired for a body part or a therapeutic device. For example, a CPAP mask is worn as an extension of the head and face. Accordingly, adjusting the fill material 28 may involve pushing, punching, patting, and otherwise exerting force to move fill 28 in a particular direction. Such may be a strike, a lifting, shaking, or the like whether light or vigorous. Adjusting 76 is similar to migrating 70. Nevertheless, migrating 70 may be thought as of the macro movement of the fill material by substantial free fall down into the particular location from which it may thereafter be adjusted 76 to fit the particular body part. Adjusting 76 involves not free falling of fill but overcoming interactions between granules flutes to move them laterally away from an area.

Ultimately, a user will position 78 the body, or a body part and then nest 80 by moving until comfort is maximized. For example, an individual may rock the head back and forth, may crane the neck forward and backward, or the like in order to form a nest of fill material 28, This provides a complete support profile in the fill material 28 under and supporting the profile of the body parts supported.

Accordingly, vertical, horizontal, whether lateral or transverse, or other pushes, strikes, shaking, rocking, or the like may be used to nest 80, typically by movement of the supported body part itself. Thus, rocking the head from side-to-side, sliding the head from side-to-side while pivoting on the neck, shrugging the shoulders, pushing the pillow into the shoulders, and the like may be used to create the indented regions 50 about the perimeter and on the top 14, as required.

It has been found, that a user may rest 82 with little or no need to further adjust 76 the pillow 10. Extended periods of rest 82 may occur by virtue of the uniformity of the support pressure. The spring-like resilience of the fill material 28 is effectively captured within various indented regions 50 on the pillow. If an individual desires to change position, a decision 84 to change may be thought of as an individual's sleeping decision. Upon changing 84 substantially the position of the user or the pillow, rest 82 may continue.

On the other hand, if the position is changed, then a yes response to the decision 84 may result in further decisions, such as incrementing 86. For example, if movement is simply an incremental movement, then a decision 86 results in a yes involving repositioning 78 the body or body member.

Likewise, if the position represents a substantial variation in the locations or shapes of the indented regions 50, then a decision 88 may determine whether to modify, such as adding, subtracting, or moving any particular support. A yes response to the decision 88 may result in additional adjusting 76 of the fill 28. Similarly, a no decision may still present the decision 90 as far as larger bodily movement.

If the body moves, and thus is reoriented 74, then an individual may re-enter the process 60 by orienting 74 the body or body member. A negative response to the decision 90 may present the optional decision 92 to change which member of the body or mode of use is employed.

For example, an individual may move from supporting a calf of a leg to a knee, to an ankle, or the like. Similarly, an individual may move from supporting the neck and head in back-sleeping mode, to supporting the shoulders, in a stomach-sleeping mode. Thus, a yes response to the decision 92 of changing the mode may result in locating 72 the pillow 10 anew.

Likewise, a negative decision 92 or a negative response to the decision 92 may still present a user with the decision to make a major change to the structure of the pillow in the decision 94. For example, a major decision 94 may be the decision to change the amount of fill material 29 in the pillow 10. Changing the fill fraction may result in returning to the determining step 64 in which a user may add or subtract material 28 from within the pillow 90.

Figure 23:
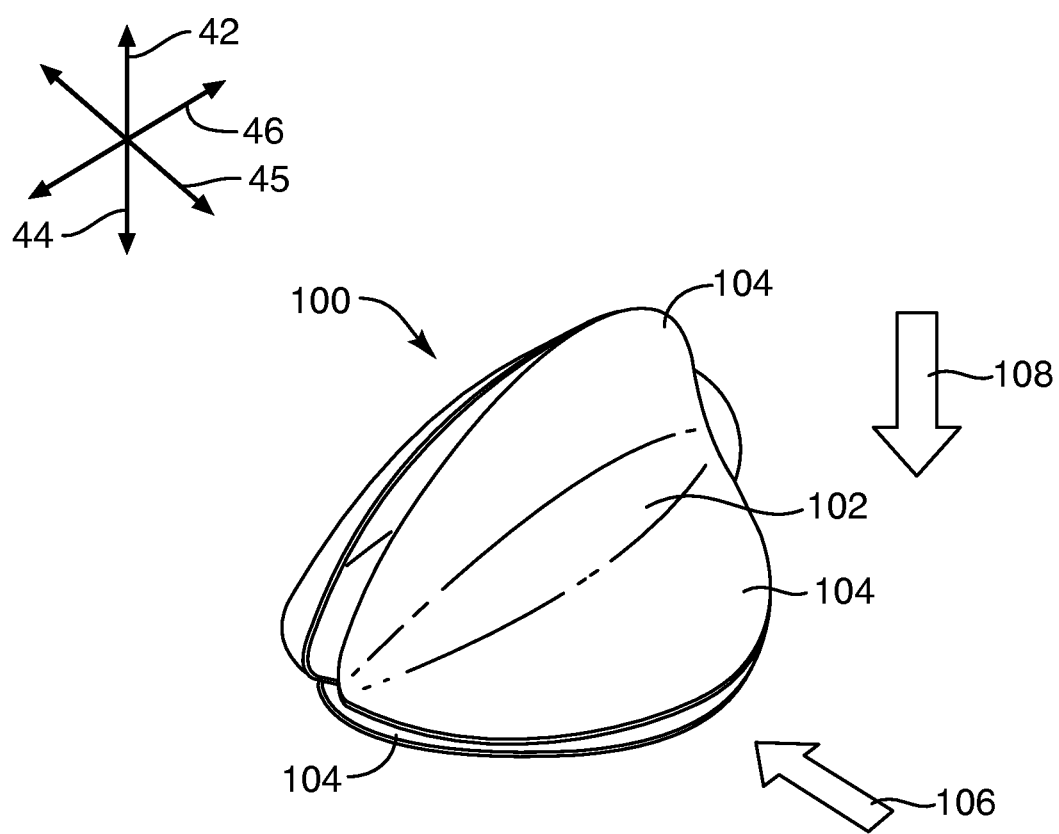
FIG. 23 is a perspective view of one embodiment of a fill material, a buckwheat hull suitable for filling an apparatus in accordance with one embodiment of the invention.
Figure 24:
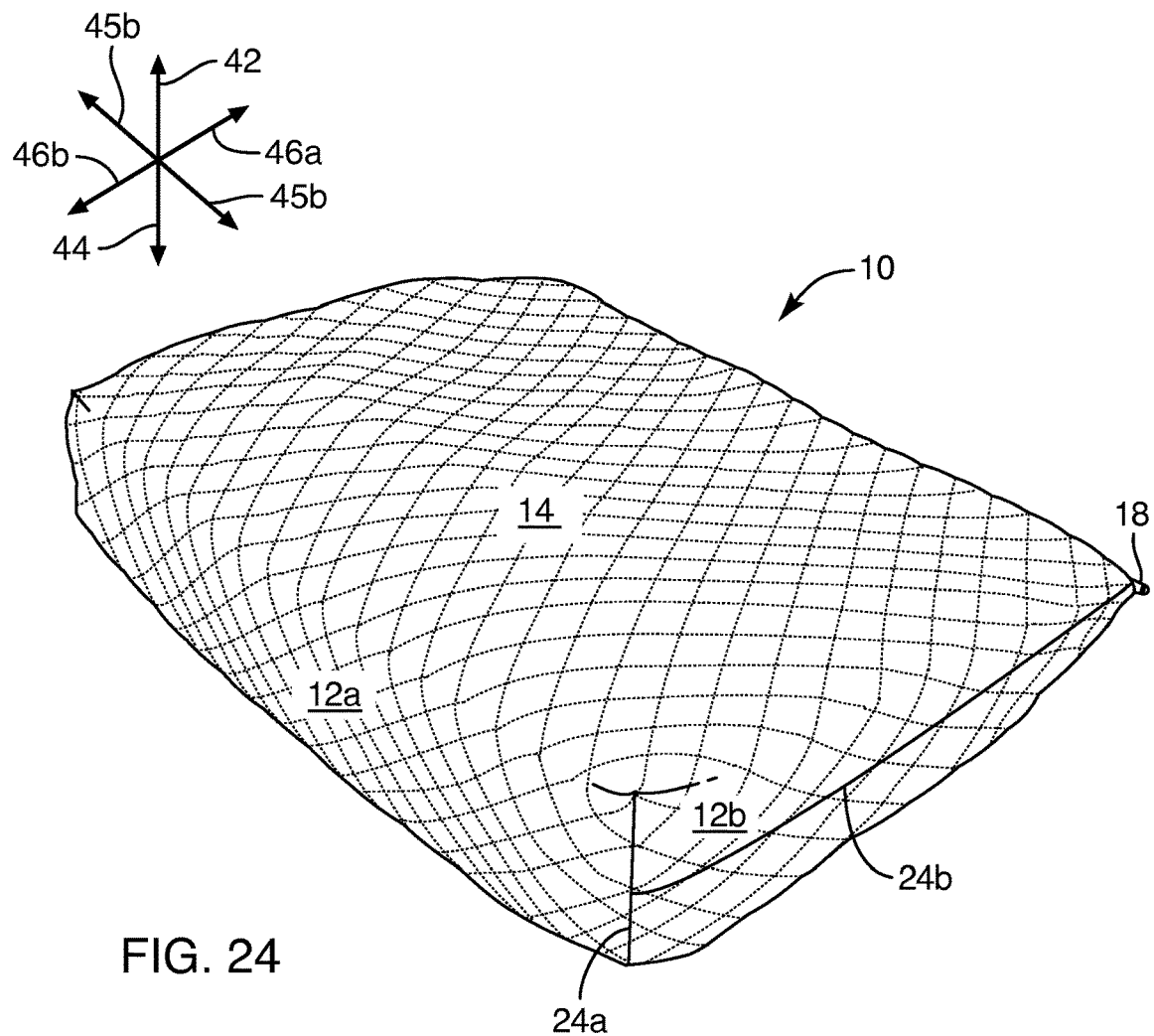
FIG. 24 is a frontal perspective view of an alternative embodiment of a pillow in accordance with the invention.
Figure 25:
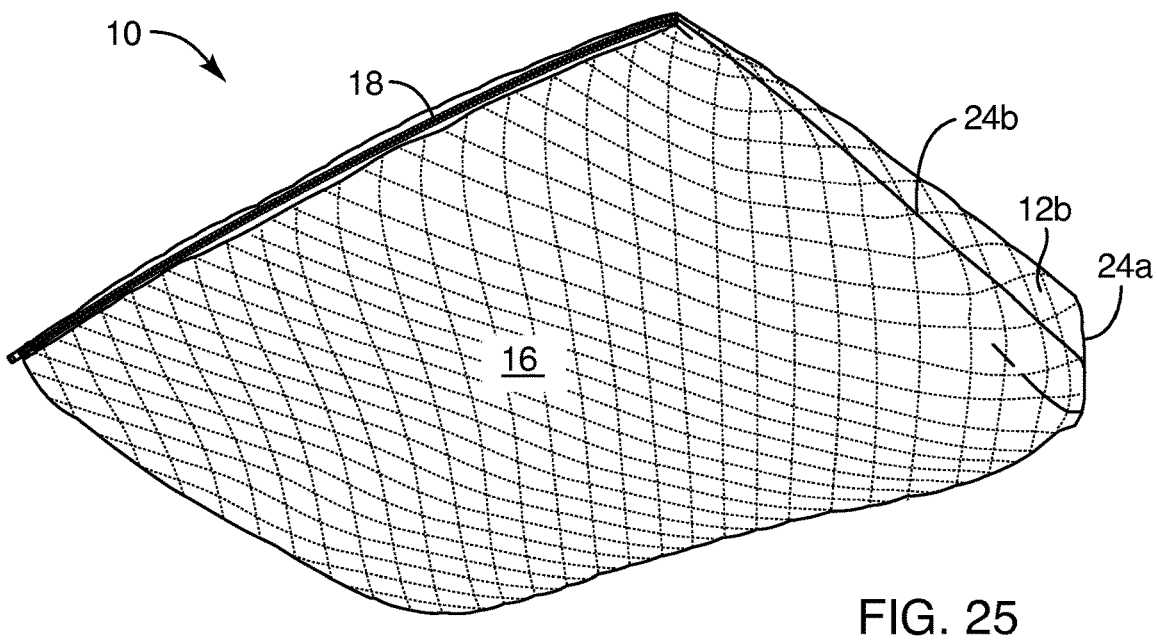
FIG. 25 is a bottom fronted perspective view thereof from the rear.
Figure 26:
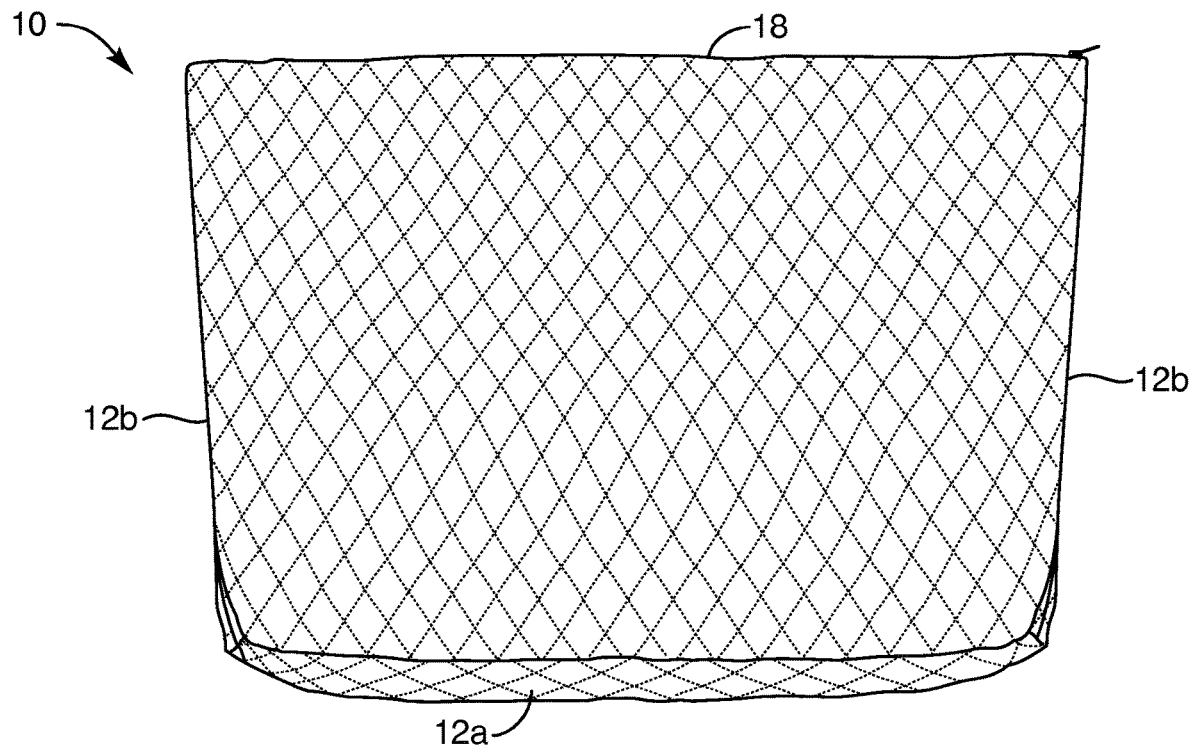
FIG. 26 is a top plan view thereof.
Figure 27:
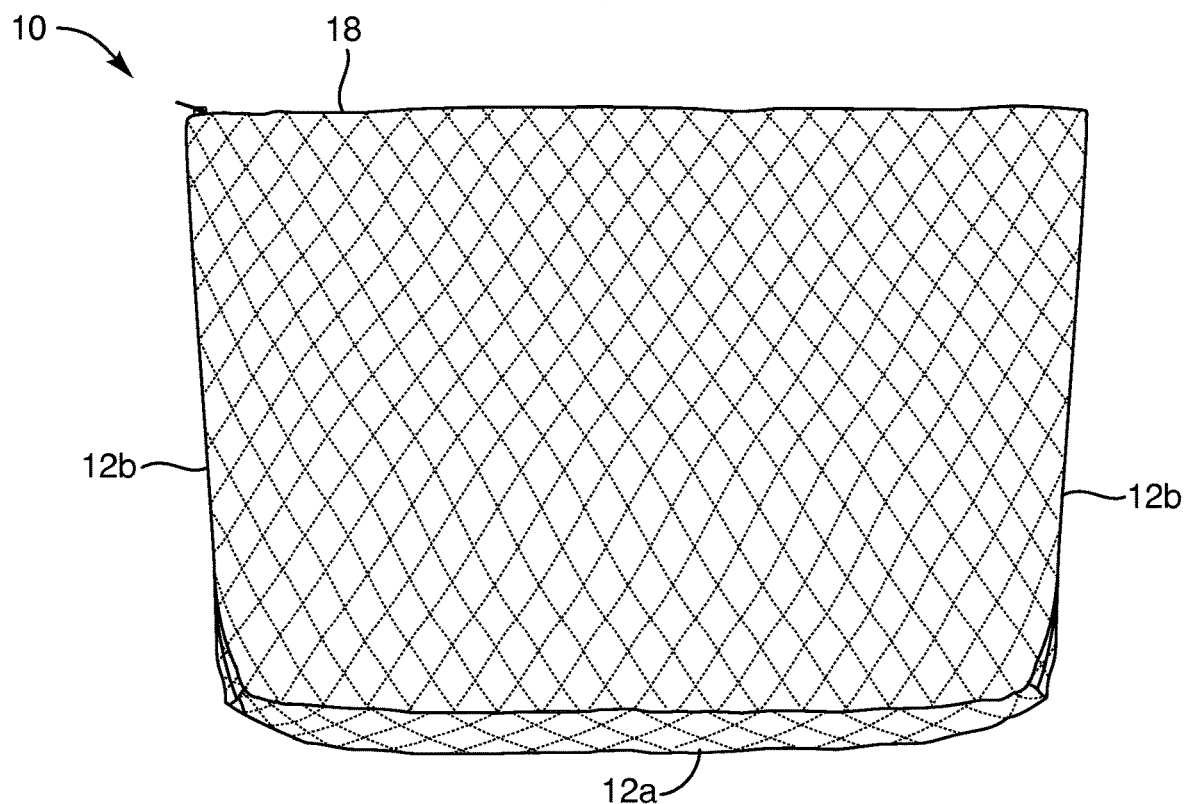
FIG. 27 is a bottom plan view thereof.
Figure 28:
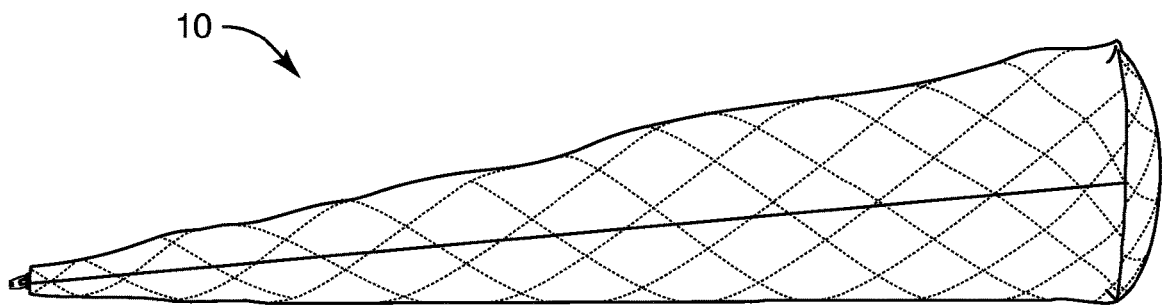
FIG. 28 is a right end elevation view thereof.
Figure 29:
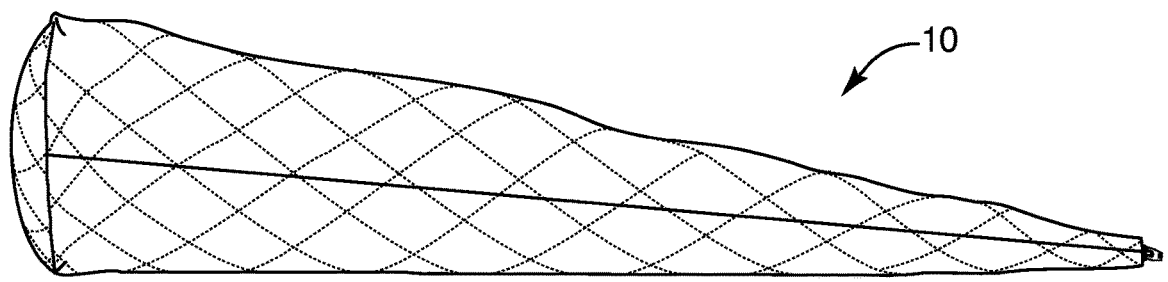
FIG. 29 is a left end elevation view thereof.
Figure 30:
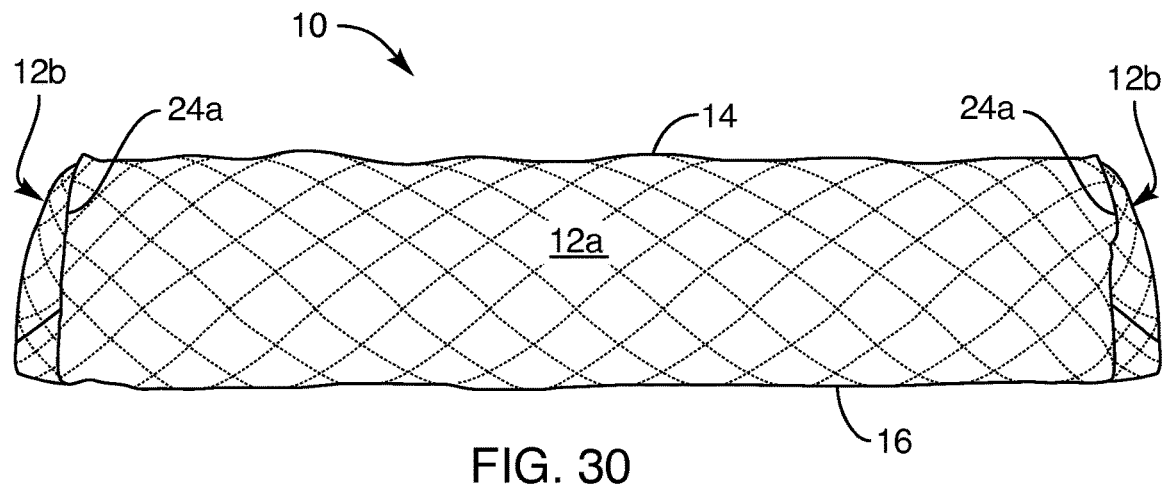
FIG. 30 is a front elevation view thereof.
Figure 31:
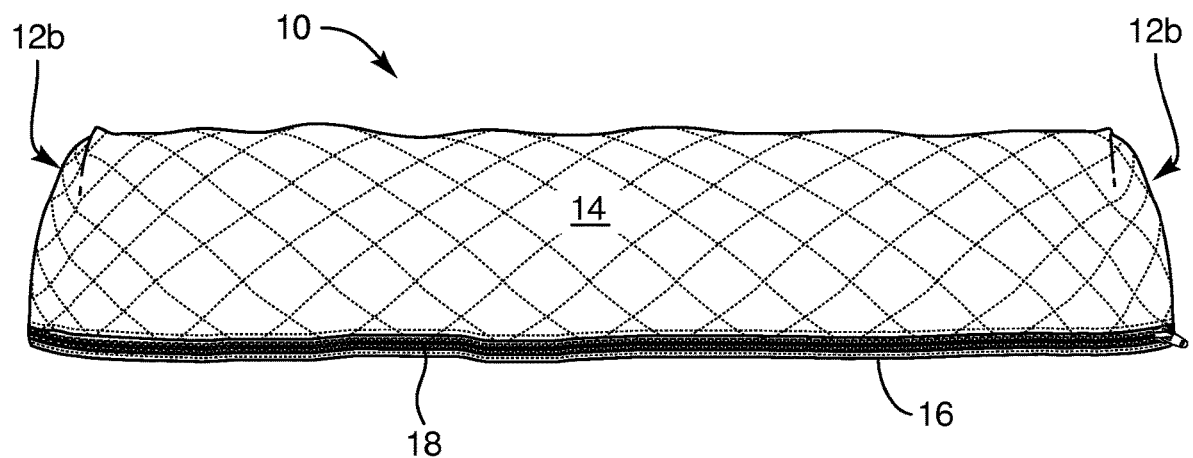
FIG. 31 is a rear elevation view thereof, wherein all of FIGS. 24 through 31 represent the actual fabric shape, if internally stiffened by supports, and represent a pattern, but do not represent the shape that the pillow will take once it is filled with filling material and is subjected to forces and shaping by a user.

Referring to FIG. 23, in one embodiment, a fill material 28 may include a buckwheat hulls. Buckwheat hulls have certain benefits of granularity, and certain benefits of mutual engagement. For example, in the illustrated embodiment, a hull 100 typically involves a core 102 with flutes 104 extending therefrom. In response to a force 108, the flutes 104 may deflect. Each has a certain resilience, much like a wooden beam or thin wooden prong on a leaf rake might bend upon being flexed.

In response to a comparatively greater force 106 applied by a user, a hull may move. Nevertheless, the flutes 104 of one hull 100 may engage the flutes 104 of another hull 100. Accordingly, a certain resistance to the force 106 maintains a certain degree of stability. Nevertheless, force 108 or weight 108, typically presented by a hand, or other bodily member of a user may also tend to elicit a spring-like response from the hulls 100 therebelow.

In the illustrated embodiment the hulls may be shaken free such that they free-fall as described with respect to FIG. 11. Nevertheless, once settled, as described with respect to FIG. 22, the fill, having migrated 70 to one side of the pillow, may later then be adjusted 76 in accordance with lifting in a vertical direction 42, or pushing down in a vertical direction 44.

Similarly, a user may push in a lateral direction 46 or transverse direction 45 in order to move the fill. Typically, a transverse or longitudinal direction 45 with respect to a user may be imposed by a shoulder abutting against the wall 12 or the frame 12 of a pillow 10. Similarly, the weight 108 of a head or neck of a user may result in a force tending to compact and engage the hulls 100 with another, with the flutes 104 acting as springs.

Thus, in general, a lifting motion or a force in a horizontal direction, in the absence of weight 108 above, or a sufficient force compressing down the hulls 100 may result in easy movement. By contrast, compressive loads, particularly when hulls 100 are supported from the sides, such as in the areas 52a, 52b, or the areas 52, in general may provide a stability and resistance to shifting of the hulls 100 out from under a bodily member of a user.

Thus, in one embodiment of an apparatus and method in accordance with the invention, buckwheat hulls 100 have been found to be very effective in that they permit the uncoupling of the spring response of the hulls 100 and their flutes 104 from the distribution and thickness determinations. As compared with conventional pillows and other prior art devices, where this uncoupling is not available, the pre-load of adjustment is uncoupled from support pressure being imposed on a bodily member.

In contrast to convention, once the pillow 10 has uncoupled, these forces the downward weight of a user 108 on the hulls 100 may result in a reduced, more distributed, spring-like resistance by deflection of the flutes 104. This provides considerable support, and may profile the full support area of a body part. This comes at a substantially uniform pressure, uniform spring constant, and beginning at a substantially zero value of force prior to weighting by the weight 108 of a bodily member of a user.

Meanwhile, lifting or any type of lateral 46 or longitudinal 45 force on the hulls 100 results in a response similar to that of a liquid. This is a flowing of the granular material, having no weight 108 to force engagement. As quicksand floats above an underground spring, the hulls 100 float above the force imposed by hand below or beside, not countered by any weight 108. Later, weight substantially above it and pressing down engages the flutes 104 with each other.

In certain embodiments, an apparatus in accordance with the invention may include buckwheat hulls captured within a side panel 12 of a pillow 10. The side panel 12 may be pre-quilted in order to provide a substantially semi-rigid material at least with respect to its own weight. That is, the material 20 has the ability to be folded, bent, and the like, but is nevertheless substantially self-supporting and thus able to maintain a shape.

Moreover, the material is quilted in order to provide silencing of sound from the movement of the hulls within the pillow 10 as well as providing isolation decoupling of the path of mechanical connection. That connection would otherwise tend to cause the material 20 of the pillow 10 to become a speaker. Transmitting mechanically the vibrations and motion of the fill material 28 inside is thus inhibited. Thus, the quilting dampens noise and uncouples, by virtue of distance, and mechanical disconnection, the generation of sound from the hulls. It also limits the generation of sound by motion of fill 28 against the material 20.

Surface softness may provide a pillowing, but also a bridging between the texture of individual hulls 100 with their flutes 104 extending therefrom. Accordingly, the quilting provides mechanical bridging between the hulls, thus eliminating or greatly reducing the texturing of the surface of the material 20, that may otherwise literally scrape, abrade, and damage the skin of a user resting there against. For example, the quilted material 20 removes localized extension of the hull flutes 104 from poking the fabric 20 outward and giving a sharp abrasive texture to the material 20 on the outside of the pillow 10.

In certain embodiments, the material of the fill 28 may include plastic granules or natural materials, such as buckwheat hulls which are light, having engagement between flutes 104 thereof, and providing a much lighter spring force or a much lower spring force for a particular displacement then would beads, beans, grains, or other smooth particles. That is, the hulls 100 themselves, even in their core 102 each have a certain amount of displacement available as a spring constant. The hulls' flutes 104 also provide, by bending and otherwise deflecting, additional spring-like displacement or deflection providing additional comfort.

In the illustrated embodiments, it has been found that the pillow 10 in accordance with the invention dissipates heat and moisture by providing substantial area between the fill granules 28 for passing moisture, air, and the like. Meanwhile, the fill material 28 itself is non-absorbent.

When compared with cervical pillows, such as are used for neck support, the provision of uniform support is typically only accomplished in the prior art by particularly complicated combinations of shapes, resilience of spring constants, and the like. All of the foregoing becomes of only limited use, inasmuch as a change in position by a user may load the neck, head, or shoulders from a completely different angle for which the specially cervical pillow or CPAP pillow may be inadequate.

By contrast, the pillow 10 in accordance with the instant invention may be readjusted at any time, by a slight adjustment 76 of the fill material 28 according to the desires of a user. Fill may be pushed into a particular location, and immediately nestled into by a body of a user by a few lateral motions, taps, pats, or the like.

Accordingly, a pillow 10 in accordance with the invention is a pillow adapted to support substantially all sleeping positions, and to any particular body part. Thus, the shape is not required to be permanently configured to the exclusion of alternative sleeping positions by a user. Prior art pillows are not well adapted to back sleeping, and typically, contain inadequate fill support in the corner regions 52 that are well filled. They do not and provide a non-pressurized reservoir of fill materials, maintaining the indented regions 50 as desired and adjusted by a user.

Referring to FIGS. 24 through 43, an alternative embodiment of a pillow 10 in accordance with the invention may benefit from a somewhat different shape adapted to the operational functionality of all the pillows 10 in accordance with the invention. In the illustrated embodiment, the side panels 12b of the pillow 10 are illustrated in a comparatively theoretical position in the illustrated embodiment. For example, the top 14, the panel 12a, and the bottom 16 are all a continuous contiguous single piece of fabric. In reality, the side panels 12b are part of the top 14 which is part of the panel 12a, which is part of the bottom 16.

A manner of manufacture is that a gusset seam 24a or simply a structural seam 24a is sewn to gather together the side panels 12b, the top 14, the front panel 12a, and the bottom 16. Similarly, a seam 24b is sewn through each end panel 12b basically forming a right angle with the seam 24a. A zipper 18 or other closure 18 seals the end or the opening of the sack or bag that forms the pillow 10. The shape of this pillow 10 is much more in accord with the actual distribution of the fill material 28 to be contained therein than some other embodiments. Likewise, the zipper 18 provides additional structural body or stiffness to support shaking the pillow 10 in order to collect all of the fill 28 near the panel 12a.

Referring to FIGS. 24 through 31, while continuing to refer generally to FIGS. 1 through 43, an apparatus and method in accordance with the invention may be sewn, and may even be templated exactly as illustrated in FIGS. 24 through 30. For example, if cardboard, wire, or other stiffeners were placed inside the pillow 10 for display, the actual shape and extent of the material 20 or fabric 20 of the pillow 10 would form the designated portions 12a, 12b, 14, 16 as illustrated.

As a practical matter, the fabric 20 of which the pillow 10 is made will necessarily conform to the fill 28 almost as if the fill 28 were a liquid in a bag 10 constituting the pillow 10. Thus, the corners or edges as illustrated in FIGS. 24 through 31 will not typically be precisely defined nor form sharp angles.

Referring to FIGS. 32A through 43, the actual more realistic view of the pillow 10 in actual use is illustrated. More will be discussed later with respect to these figures. One may see that FIGS. 24 through 31 represent a rather theoretical, although actual spatial extent of the fabric 20 of which the pillow 10 is made. They do not represent the disposition or actual shape of the pillow 10 that will exist once the forces and volumes associated with the fill 28 and a user are applied to the pillow 10.

Referring to FIGS. 24 through 43, one may see that the panels 12a, 12b that form the "frame 12" of the pillow 10 in accordance with the invention provide for a more-or-less triangular end panel 12b. The manufacturing is simplified by the seam 24a or gusset seam 24a that connects the top 14 and bottom 16 to one another, and extends therebetween. It is also connecting the end panel 12b to the panel 12a.

The zipper 18 or other closure is well adapted, and may be provided with internal linings, such as an extension that is provided additional fabric, possibly folded to be expandable, for covering the gap opened by the zipper near each end in order to facilitate opening of the zipper 18. The extensions block any escape of the fill material 28 through the corners or the end connection locations of the zipper 18 to the pillow 10.

Figure 32A:
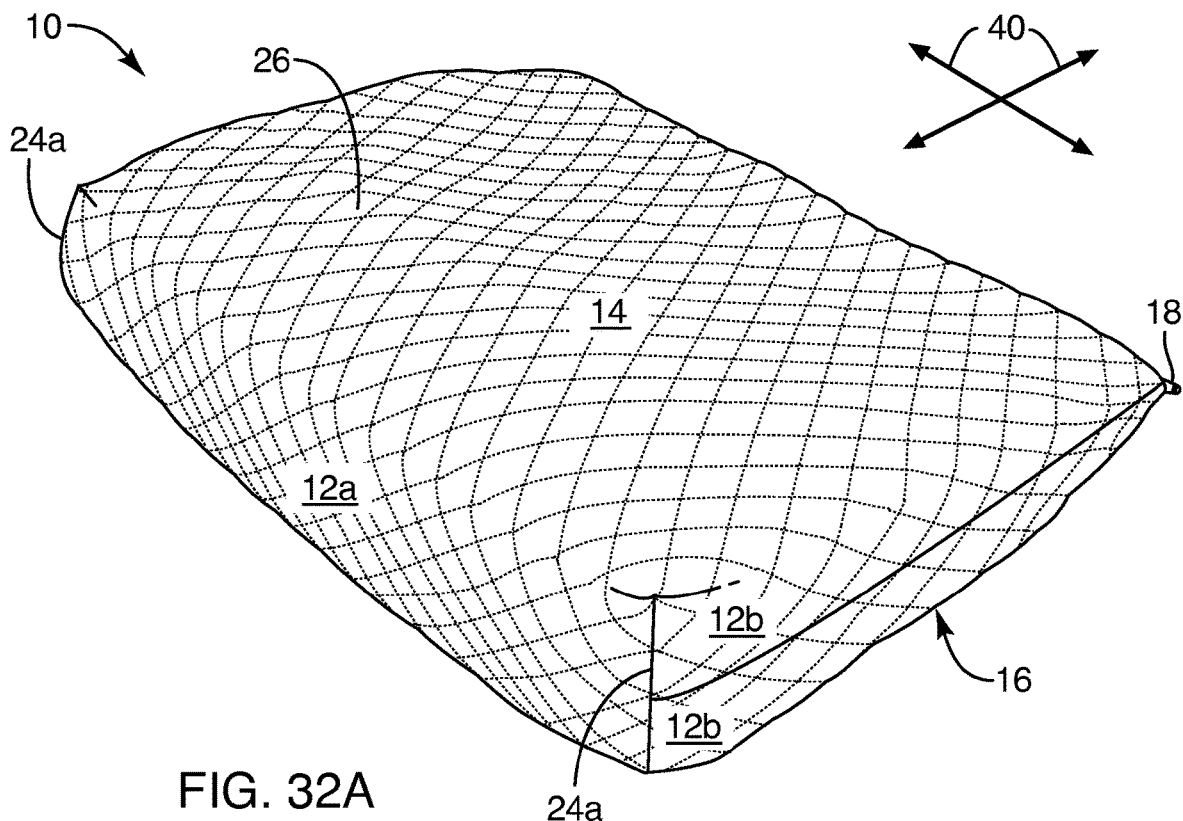
FIG. 32A is a frontal perspective view of a pillow in accordance with the invention having fill material therewithin, and thus affecting the shaping thereof.
Figure 32B:
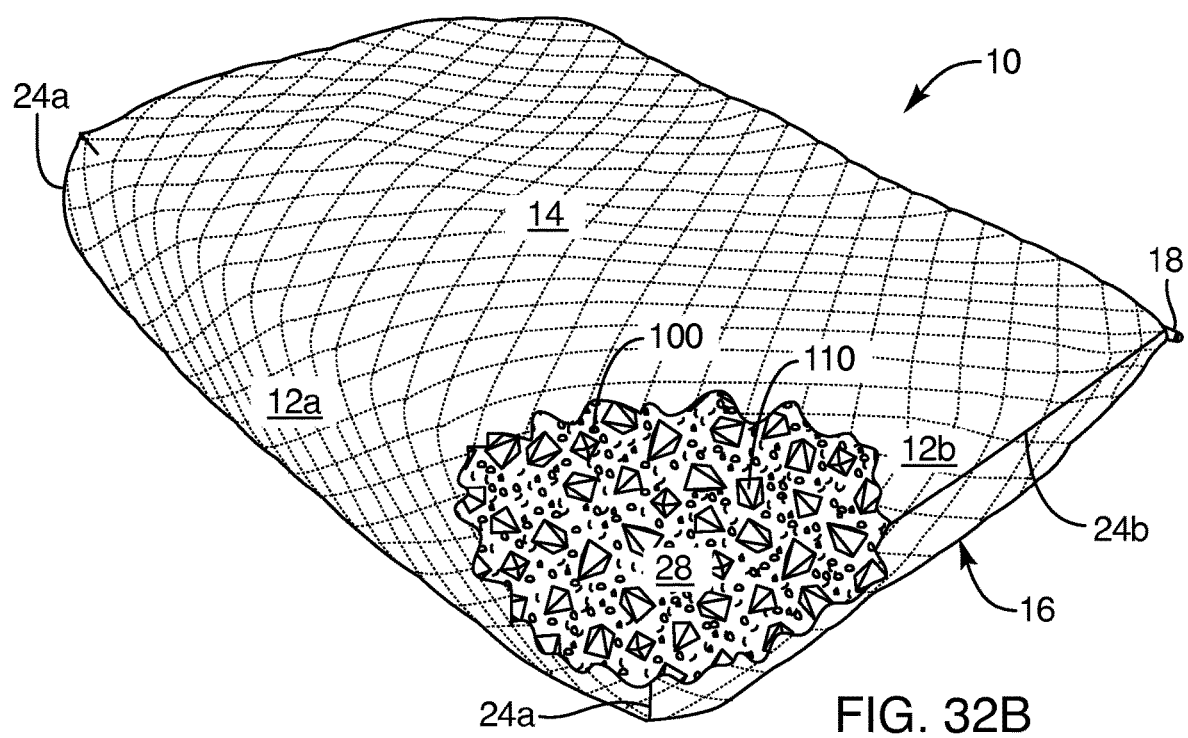
FIG. 32B is a frontal perspective view thereof, partially cut away to show the alloyed fill material comprising a combination of a small granular material, such as buckwheat hulls, and a larger resilient, "chunk" material having a smaller spring constant than the granular material, a larger displacement, and constituting a minor fraction of the overall fill material.
Figure 32C:
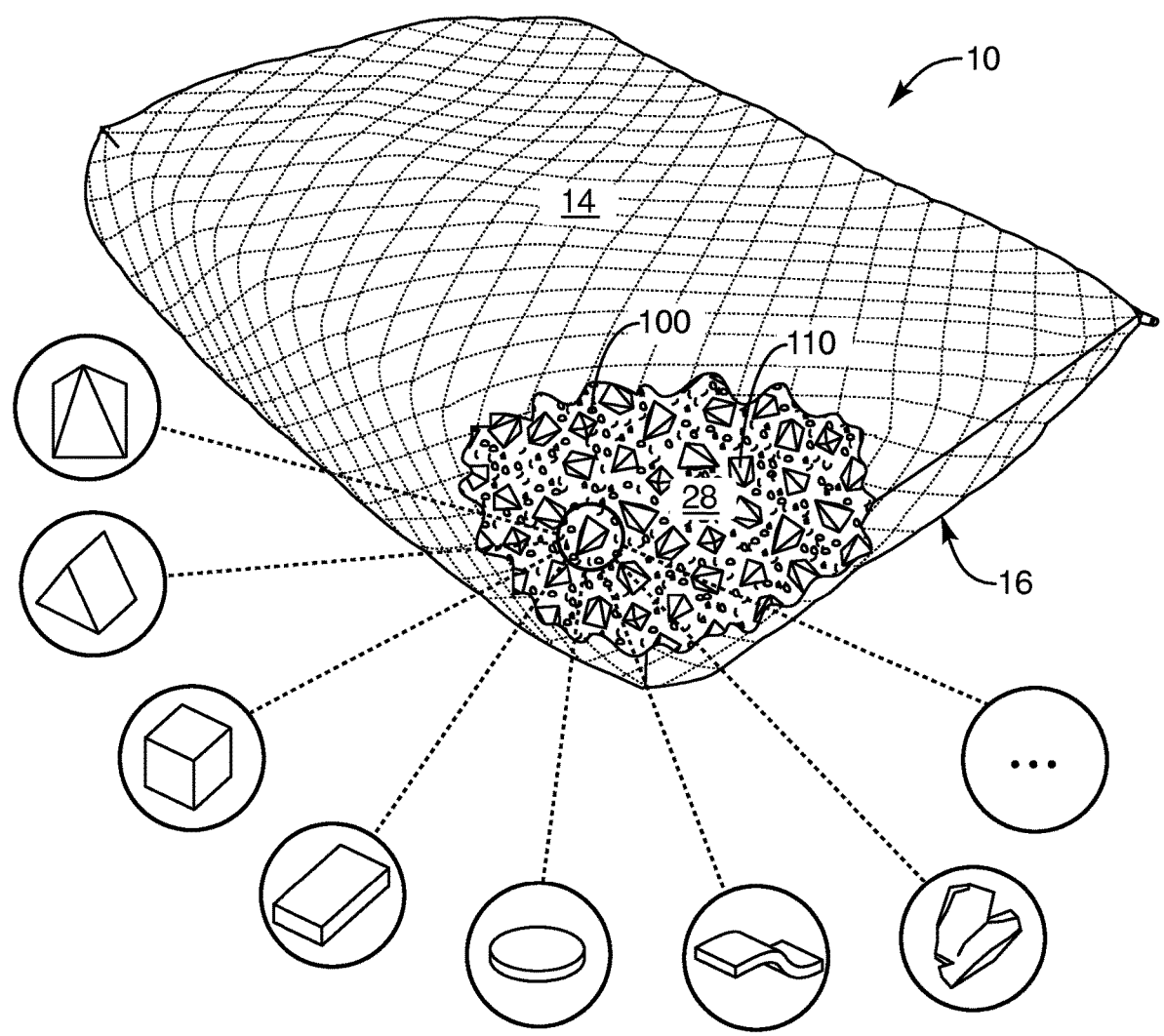
FIG. 32C is the same frontal perspective view as FIG. 32B, showing several alternative shapes for the larger fill material.
Figure 33:
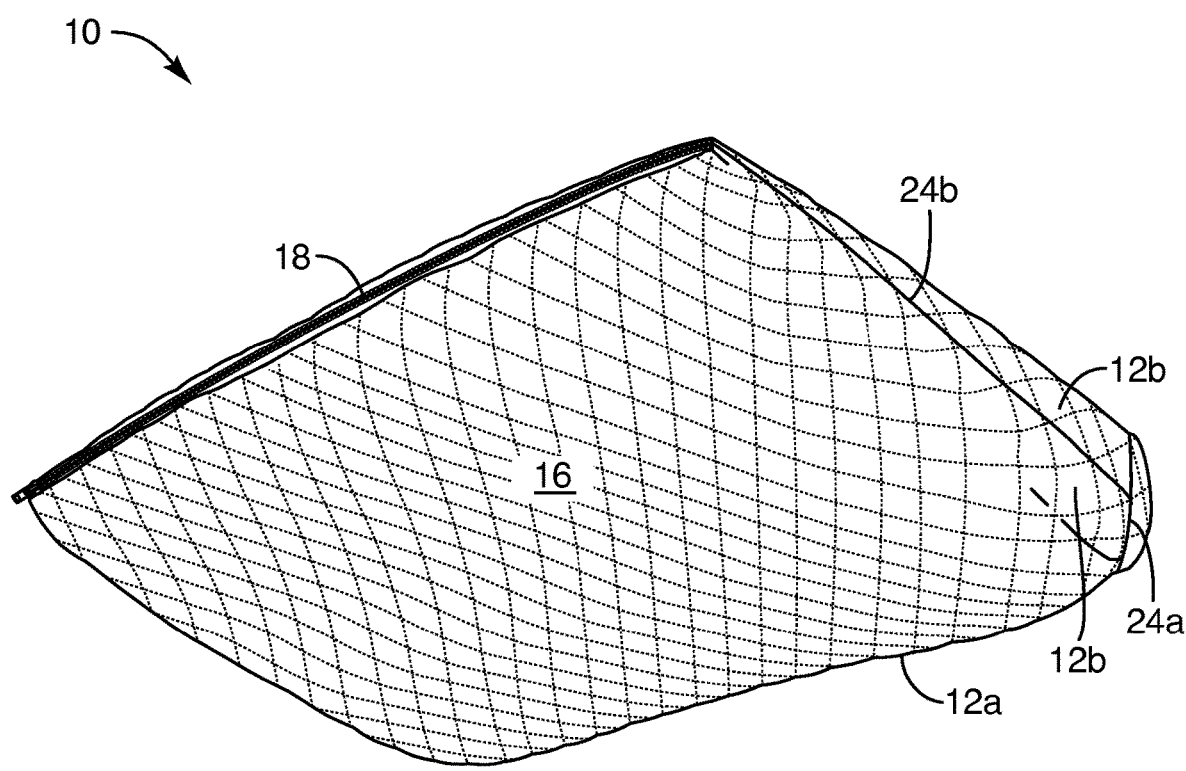
FIG. 33 is a rear, underside perspective view thereof.
Figure 34:
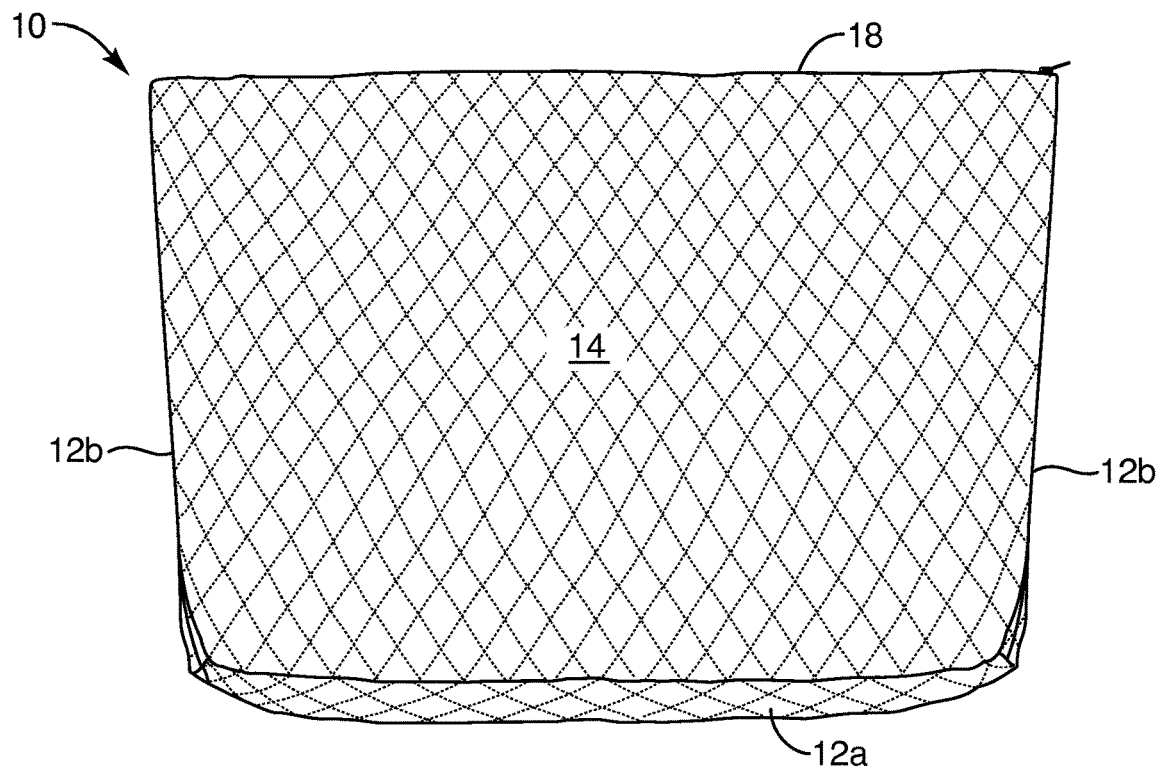
FIG. 34 is a top plan view thereof.
Figure 35:
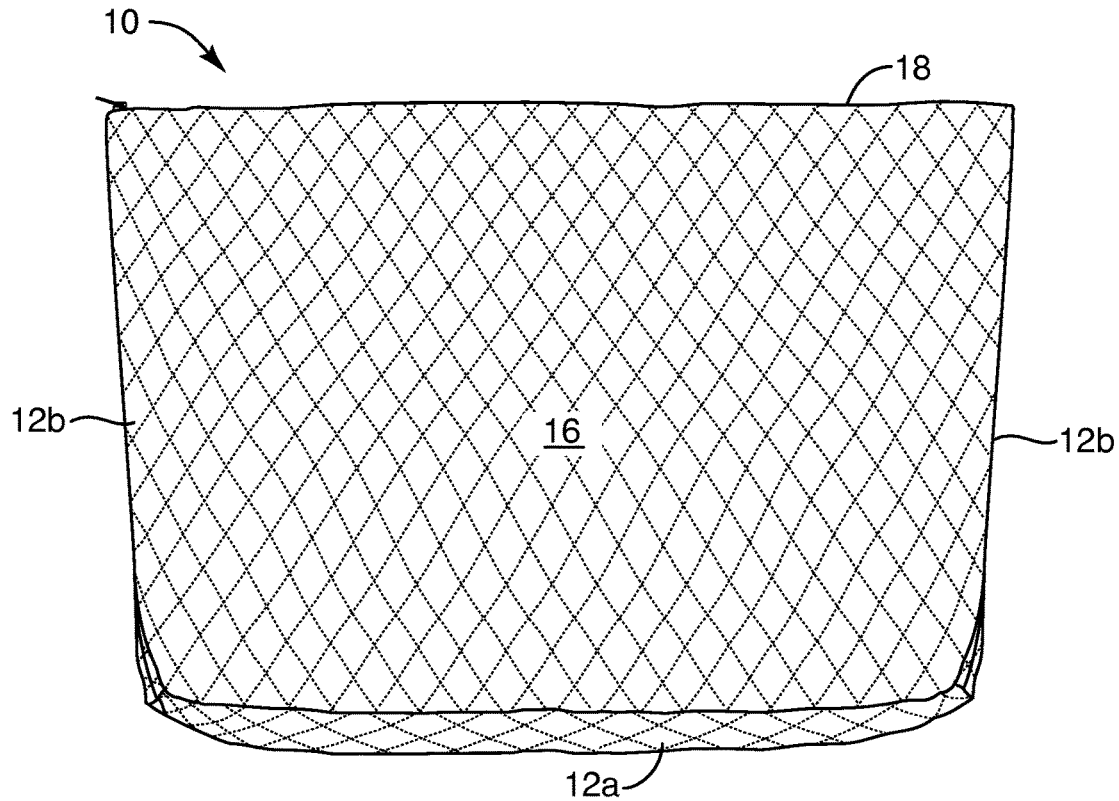
FIG. 35 is a bottom plan view thereof.
Figure 36:
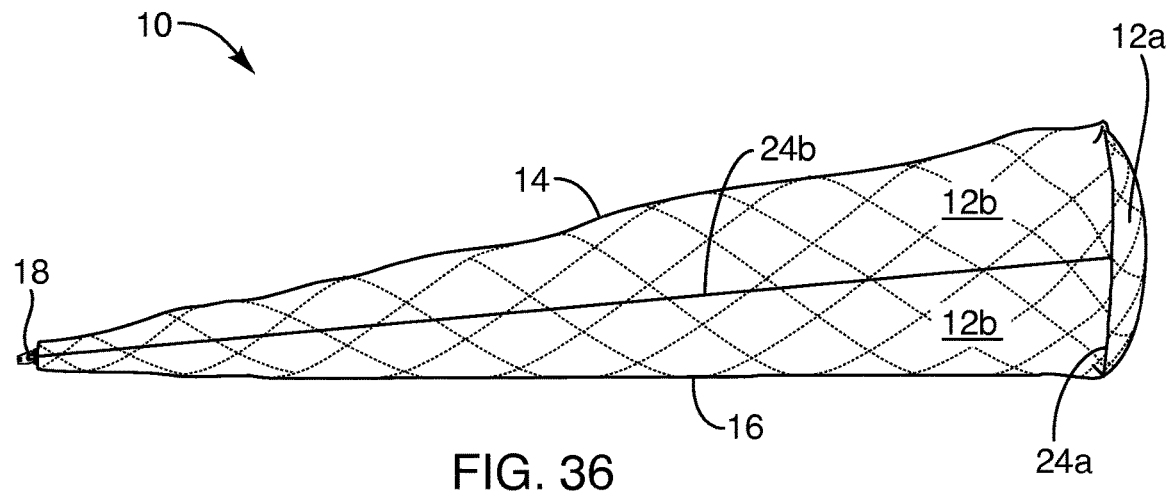
FIG. 36 is a right end elevation view thereof.
Figure 37:
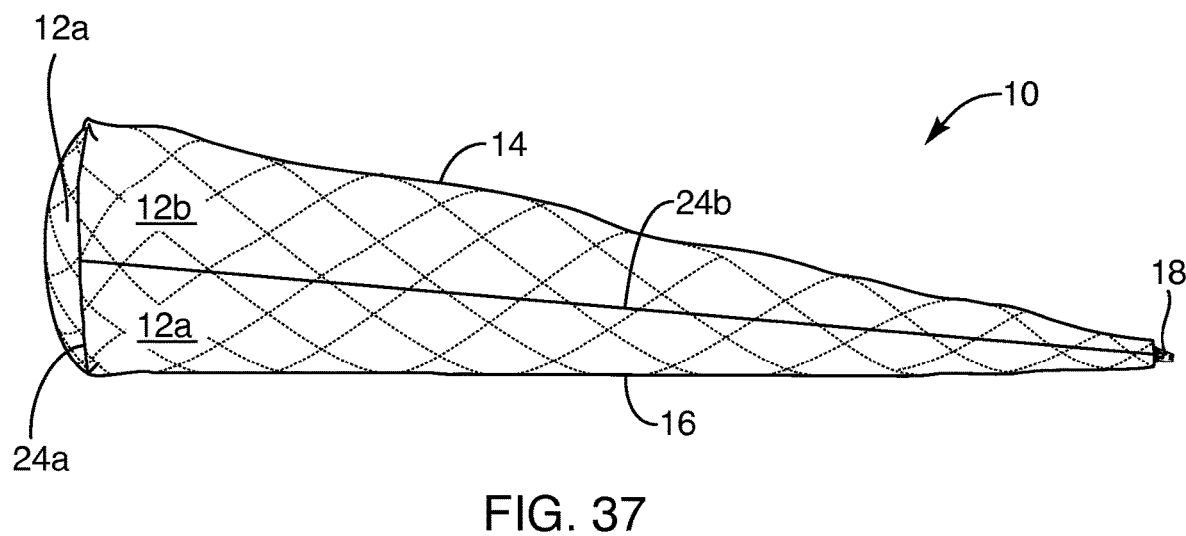
FIG. 37 is a left end elevation view thereof.
Figure 38:
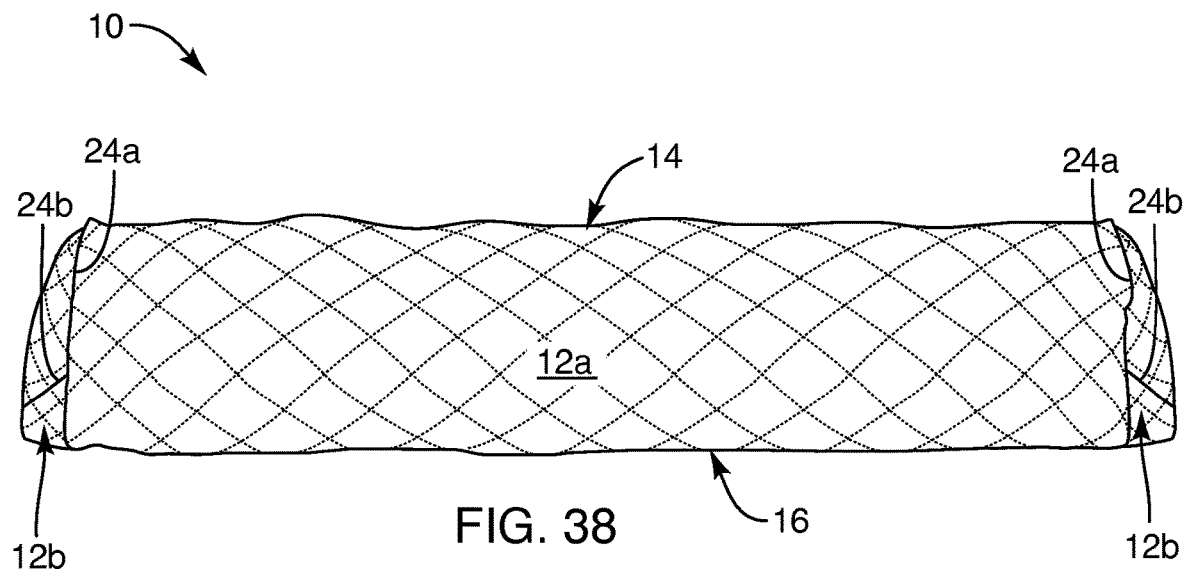
FIG. 38 is a front elevation view thereof.
Figure 39:
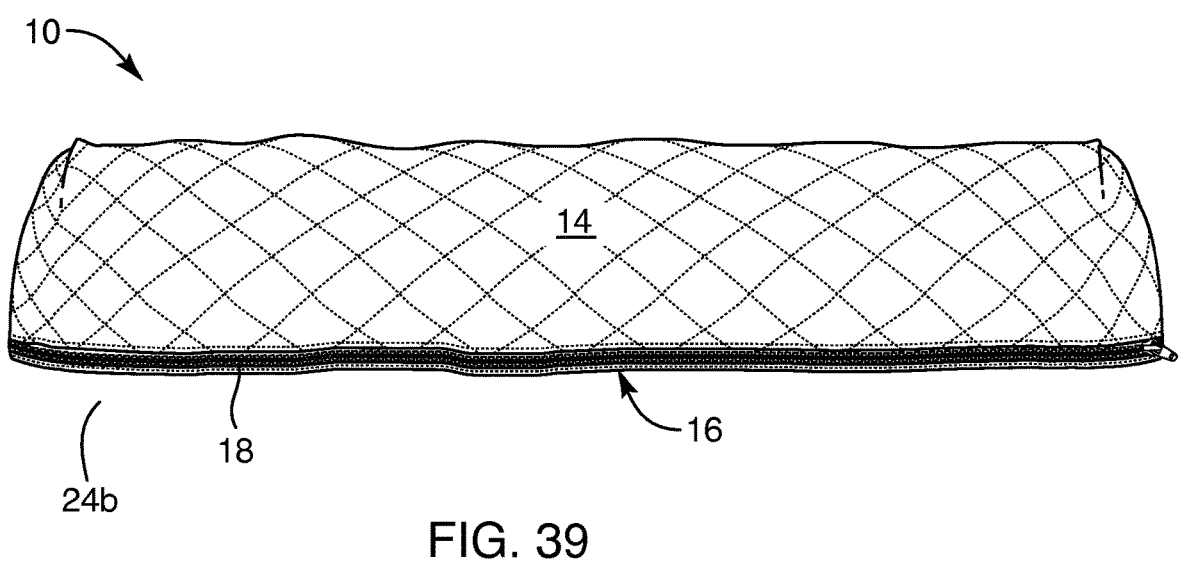
FIG. 39 is a rear elevation view thereof.

Referring to FIGS. 32A through 32C, and more generally to FIGS. 24 through 43, in one embodiment of the pillow 10 in accordance with the invention, a pillow 10 may be filled with a fill material 28 composed of both granular material 100 such as buckwheat hulls 100, and a resilient expanded polymeric material 110, such as an elastomeric foam 110 or an expanded elastomer 110. In certain embodiments, discrete pieces of a common polyurethane foam 110 or chopped foam 110 serve well.

Typically, a mean diameter may be defined for any material 28, 100, 110 as the wetted perimeter four times the area divided by the wetted perimeter. This is referred to as a hydraulic diameter. It also serves well to characterize any material 28, 100, 110 of irregular shape or size, and herein is referred to as an effective diameter.

In the illustrated embodiment, it has been found that from about five percent to about 35 percent (by volume) of the larger-sized material 110, will work. Typically an expanded, elastomeric material 110 (elastomeric foam 110) will have a median size (effective diameter) of from about one centimeter to about five centimeters. The targeted, mean effective diameter will typically be on the order of about an inch (2½ cm) or more. However, there may be a distribution of sizes.

It is typical that the mean diameter or the mean effective diameter of the foam material 110 is about an order of magnitude (ten times) or more greater than that of the granular material 100. In the illustrated embodiment, buckwheat hulls 100 may be distributed in foam 110, or vice versa in a ratio of from about five percent to about 35 percent (by volume) large resilient components 110 and from about 75 to about 95 percent the granular material 100. A target or operational characteristic of about ten to 20 percent of the larger constituents 110 compared to the overall total volume has been found to be very effective.

The operation of the fill 28 in accordance with the illustrated embodiment provides additional benefits over certain embodiments described hereinabove. For example, in certain embodiments, the larger fill material 110 may be constituted by strips of fabric. Strips having a thickness of common fabric, or a batting material such as a quilt batting, may be formed to have a thickness of the fabric as it comes from a factory ranging from about $\frac{1}{32}$ inch or less up to about ⅛ to ½ inch. A thickness of about ⅛ inch has been found to be a good target number for the thickness dimension.

Meanwhile, the fabric or other strip material used as the larger constituents 110 may be from about half a centimeter wide to about three centimeters wide, with a target of about two centimeters in width. Lengths may vary from about two inches to about six inches, or even nine inches. Typically, a target may be a batting material 110 having a thickness of about ⅛ inch, a width of about two centimeters, and a length of about four. It has been found that the batting material used as the larger constituent 110 or the larger-sized constituent 110 tends to make a more dense pillow. Also, batting has very little resilience. Upon application of a force, even the weight of the granular material 100 thereon, batting tends to collapse.

However, the stabilization is very effective. That is, the larger-sized constituent 110 operates as an alloying material. Stated another way, the granules 100 have a certain tendency to interlock with one another in a pillow 10 in accordance with the invention, as described hereinabove. However, some sleepers who tend to be "restless sleepers" have more activity during the nighttime. This results in more movement of the head and neck of a user, resulting in more distribution and flattening of the fill 28 generally. The presence of the larger-sized constituent 110 operates to resist large migrations (on the order of the distance between adjacent pieces 110) with a single movement.

Lifting the pillow 10 by the zipper 18, and shaking the fill material 28 toward the panel 12a still serves equally well. In free fall, the fill material 28 will fall. However, when the bottom 16 of the pillow 10 is resting on a supporting surface, and a user is resting a head, neck, shoulders, or a combination or subcombination thereof on the top 14, the fill 28 will not, and indeed cannot, migrate as easily in response to motion and force applied by a user. Thus, the larger-sized constituent 110 operates as a dam, blocking, resisting, and re-directing migration or flow of the granular material 100.

As a practical matter, as to blocking the granular material 100 against easy migration, the strip-type material, such as a quilt batting, and the chopped foam material 110 operate satisfactorily. However, it has been found that the resilience of the foamed material 110 or chopped foam 110 is considerably lighter. Occupying from about ten to about 25 percent, and having a target of about 20 percent of the overall volume of the fill 28, provides additional resilience, and a significant reduction in density of the fill 28.

Since the volume of elastomeric foam 110 constitutes mainly air, the effective density of the fill 28 is reduced by the use thereof. Moreover, since the elastomeric foam 110 has a greater spring constant than batting 110, it will tend to expand to fill its available space in the presence of the granular material 100.

However, any batting 110 has a lower spring constant than the elastomeric foam 110. The granular material 100, such as buckwheat hulls 100 has a greater spring constant than either one. Thus, the buckwheat hulls 100 are the stiffest, speaking of the spring constant or the ability to deflect under load, while the foamed elastomer 110 has the next lowest spring constant, while any batting 110 has the lowest spring constant. Thus, it has been found most effective to use expanded elastomeric materials 110 as the larger-sized constituent 110, and buckwheat hulls 100 as the granular material 100.

The pillow 10 lacks any significant mechanical rigidity out of the plane 33 or parallel direction 40 with respect to the fabric 20 of which the panels 12, 14, 16 are formed. It bends. The pillow 10 absent the fill 28 will simply flatten, droop, or otherwise deform to some equilibrium position from the force of its own weight. However, with the fill 28 installed inside the pillow 10, the pillow 10 tends to have the shapes illustrated in FIGS. 32A through 43.

One will note that the top 14 is continuous and contiguous with both the end or side panels 12b and the front panel 12a, which also connect to the bottom 16. As a practical matter, the fabric 20 will flex out of the plane direction 40 of its surfaces quite freely. However, within the planar direction 40 of the fabric 20, the fabric is constrained by the threads therein to not stretch excessively or to stretch comparatively little, if at all. Thus, the pillow 10 takes on the shape illustrated.

The gusset seam 24a at the corners of the pillow 10 forms a connection, but merely provides additional continuity, with additional space for the corners to hold more of the fill 28. In contrast, near the zipper 18 or other closure 18 (where a zipper 18 is used as an example for any and all closures 18), the top 14, bottom 16, side panels, and the seam 24b in the side panel 12b create a comparatively small volumetric capacity. However, there is no real need in that location to support or contain any significant amount of the fill 28. Moreover, the shape illustrated tends to further encourage the maintenance of the fill material 28 closer to the panel 12a, without forcing it to be there in the presence of the force 106 or weight 108 applied by a user.

Referring to FIG. 40, while continuing to refer generally to FIGS. 1 through 43, a user may grip the edge (e.g., where the closure 18 is located) and lift the pillow 10 in the air. The fill material 28 will immediately freefall toward the panel 12a, which appears to be structurally indistinguishable from the top 14 and bottom 16 of the pillow 10, there being no seam therebetween. Meanwhile, the fill 28 freefalls towards the panel 12a, filling the pillow 10 to bulging.

Ultimately, a boundary 112 or interface 112 between the free air or the free region 114 of the pillow 10 and the filled region 116 thereof. As described hereinabove, the fill 28 operates similarly to that described with respect to other embodiments. Meanwhile, a user may then, having adjusted the location of the fill 28, lay the pillow 10 on a supporting surface, such as a bed.

Referring to FIG. 41, the pillow 10 laid on a supporting surface, or with the bottom 16 thereof on a supporting surface looks in cross-section like the illustrated embodiment. The boundary 112 shifts somewhat with gravity causing some slumping of the fill material 28 along the bottom 16. Necessarily, a certain amount of the fill 28 near the boundary 112 from the bottom 16 to the crest 118 will slump away.

As described hereinabove, once a user places a bodily member near the center of the pillow 10, the fill 28 will migrate. The fill 28 will migrate less, and only in response to a greater force due to the presence of the larger-sized fill material 110. Nevertheless, the fill material 28 will migrate, lift, and tend to fill up the region nearest the gusset seams 24a near the corners of the pillow 10. A certain amount of the fill 28 will also be pushed back away from the panel 12a and toward the zipper edge 18 of the pillow 10.

Referring to FIG. 42, this distribution in the ends is shown in cross-section, as only slightly different from that of FIG. 41, but with the ends more filled, and more of the material 28 migrating back toward the zipper 18 or other closure 18.

Referring to FIG. 43, near the center line or center plane of symmetry of a user, is by implication, the center plane or center line of the pillow 10. The profile, along the length of a user, of the indentations 50 or indented regions 50 is illustrated. In particular, the indented region 50a supporting the neck of a user, the indented region 50b supporting the head of a user, and the indented region 50e supporting the shoulders near the neck of a user are illustrated.

In the illustrated embodiment, it has been found that the smaller spring constant or lower value of the Hooke's-law spring constant provides an additional deflection of the pillow 10 under the weight 108 of a user thereagainst. Thus, the high spring constant and thus comparative stiffness of the granular material 100 is ameliorated by the presence of the lower spring constant and the approximately 20 percent targeted volume of the fill 28 being the elastomeric foam 110. Thus, the softness and compliance desirable in elastomeric foam 110 is achieved, without the high pressure, large volume, or the like of a conventional synthetic foam pillow.

Meanwhile, the support of the granular material 100 is available, but its migration is inhibited substantially by the presence of the elastomeric foam 110 damming, resisting, and re-directing against excessive migration the granular material 100, such as the buckwheat hulls 100. The inset image illustrates the difference in spring constant ($K_1$, $K_2$) between the two materials 100, 110. The material 110 is much more compliant, providing a certain amount of deflection, with its associated resilience or spring response.

Thus, with compression, the spring constant of the elastomeric foam 110 will resist the force 108. However, elastomeric foam 110 may actually bottom out where the pressures are comparatively higher and expand where lower. This provides the reliable resistance and support of the granular material 100 provides. Again, hitting the pillow 10 with a fist, a palm, or tapping the pillow 10 with a bodily member, such as a head of a user, one may overcome the resistance to flow, and enforce a certain amount of flow including moving the pieces 110 in order to migrate the fill 28 farther and make a preferred shape for the indentations 50.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A method of distributing pressure on a user of a pillow, the method comprising:
    providing a shell having a top and bottom substantially rectangular and connected by a wall to define only one cavity therewithin extending in longitudinal, lateral, and transverse directions, mutually orthogonal;
    providing a fill comprising a mixture of first granules, having flutes interlocking with one another absent a threshold level of stress therebetween having a first value sufficient to cause relative motion therebetween, and second granules, comparatively larger and softer than the first granules and intermixed therewith to operate to further resist the relative motion therebetween by raising to a second, higher, value the threshold level of stress required;
    filling partially the cavity with the fill;
    placing the shell as partially filled under the head and neck of a user; and forming a recess in the top by applying the second, higher value of the threshold level of stress to the mixture; and
    stably supporting, continuously and contiguously by the fill, the head and neck of the user.

2. The method of claim 1, comprising supporting a shoulder of the user continuously and contiguously with the head and neck of the user.

3. The method of claim 2, comprising forming the recess to be conformal with a shape of the head and neck of the user.

4. The method of claim 3, comprising forming the recess to be conformal with the head, neck, and a shoulder of the user simultaneously.

5. The method of claim 1, comprising applying the second, higher value of the threshold level of stress by applying compression to the top.

6. The method of claim 5, comprising exceeding the second, higher value of the threshold level of stress by applying an impact to the top.

7. The method of claim 1, wherein the second value is selected to move the mixture in the longitudinal, lateral, and transverse directions in response to forming the recess.

8. The method of claim 1, wherein forming the recess comprises positioning the back of the head of the user closer to a level of a sleeping surface under the pillow than a position of the neck of the user.

9. The method of claim 1, comprising reducing the first value and the second, higher value to substantially zero by freefalling the fill inside the shell.

10. A method comprising:
    providing a pillow comprising a shell, defining a cavity and longitudinal, lateral, and transverse directions, mutually orthogonal, and formed of a top, bottom, and wall connecting therebetween;
    providing a fill comprising a mixture having first granules and second granules larger and softer than the first granules, thoroughly mixed in a pre-selected proportion effective to establish a first value of a threshold force required to impart relative motion between the first granules alone, and a second value, greater than the first value, required to impart relative motion to the first and second granules in the mixture;
    placing a quantity of the fill in the cavity;
    reducing the threshold force to substantially zero by freefalling the quantity of the fill in the shell;
    placing the pillow on a sleeping surface;
    forming a recess substantially continuously conformal to and along a user's head and neck by applying the threshold force; and
    stably supporting, by the fill, the head and neck of the user during sleep.

11. The method of claim 10, comprising flowing temporarily by the first and second granules in response to the threshold force.

12. The method of claim 11, comprising applying the threshold force by applying impact loading to the top.

13. The method of claim 12, comprising stabilizing by the fill to support the head, neck, and a shoulder of the user in response to cessation of the threshold force.

14. The method of claim 10, comprising forming the recess conformal to the head, neck, and a shoulder of the user.

15. The method of claim 14, wherein the recess is continuously conformal from the shoulder to the crown of the head of the user.

16. The method of claim 10, wherein applying the threshold force comprises applying compression against the top.

17. The method of claim 10, wherein forming the recess comprises moving the fill laterally and longitudinally away from the recess.

18. The method of claim 10 comprising reducing the threshold force to substantially zero by freefalling the fill in the cavity.

19. A method comprising:
    providing a pillow comprising
    a shell defining a cavity formed to contain a fill, and having a longitudinal direction, a lateral direction, and a transverse direction, orthogonal to each other,
    the shell, further comprising a top, a bottom, a first wall connecting and spacing apart the top and bottom, and a joinder connecting the top and bottom together opposite the first wall, and
    the fill, comprising a mixture of a first filler and a second filler, the first filler comprising a granular material having an effective diameter less than an effective diameter of the second filler, and the second filler having a spring constant less than a spring constant of the first filler;
    placing the pillow on a sleeping surface;
    adjusting a shape of the pillow conformal to a user by applying a threshold level of force by a portion of the user against the top, the threshold level of force being selected to be effective to overcome a resistance of the second filler to flow of the first filler in response to loading; and
    conserving, by the second filler, positioning of the first filler and second filler, by resisting flow of the first filler to a weight of the portion of the user at less than the threshold level of force.

* * * * *